United States Patent
Eboigbodin et al.

(10) Patent No.: US 11,180,787 B2
(45) Date of Patent: Nov. 23, 2021

(54) STRAND-INVASION BASED DNA AMPLIFICATION METHOD

(71) Applicant: AIDIAN OY, Espoo (FI)

(72) Inventors: Kevin Eboigbodin, Masala (FI); Mirko Brummer, Lohja (FI)

(73) Assignee: AIDIAN OY, Espoo (FI)

(*) Notice: Subject to any disclaimer, the term of this patent is extended or adjusted under 35 U.S.C. 154(b) by 577 days.

(21) Appl. No.: 15/316,047

(22) PCT Filed: Jun. 3, 2015

(86) PCT No.: PCT/EP2015/062430
§ 371 (c)(1),
(2) Date: Dec. 2, 2016

(87) PCT Pub. No.: WO2015/185655
PCT Pub. Date: Dec. 10, 2015

(65) Prior Publication Data
US 2017/0096694 A1 Apr. 6, 2017

(30) Foreign Application Priority Data
Jun. 5, 2014 (GB) .................................... 1410022

(51) Int. Cl.
*C12Q 1/68* (2018.01)
*C12P 19/34* (2006.01)
*C12Q 1/6844* (2018.01)

(52) U.S. Cl.
CPC ............ *C12P 19/34* (2013.01); *C12Q 1/6844* (2013.01)

(58) Field of Classification Search
CPC .............................. C12P 19/34; C12Q 1/6844
See application file for complete search history.

(56) References Cited

U.S. PATENT DOCUMENTS

| | | | |
|---|---|---|---|
| 5,925,517 A | 7/1999 | Tyagi et al. | |
| 6,432,642 B1 | 8/2002 | Livak et al. | |
| 6,596,486 B2 | 7/2003 | Frank-Kamenetskii et al. | |
| 7,241,596 B2 | 7/2007 | Mayrand | |
| 7,435,561 B2 | 10/2008 | Piepenburg et al. | |
| 7,824,890 B2* | 11/2010 | Hoser | C12Q 1/682 435/91.2 |
| 9,062,344 B2* | 6/2015 | Hoser | C12P 19/34 |
| 10,227,660 B2* | 3/2019 | Filen | C12Q 1/689 |
| 2005/0112631 A1* | 5/2005 | Piepenburg | C12Q 1/6844 435/6.14 |
| 2005/0214809 A1 | 9/2005 | Han | |
| 2007/0054296 A1 | 3/2007 | Piepenburg et al. | |
| 2012/0157333 A1 | 6/2012 | Kauppinen | |
| 2013/0178397 A1* | 7/2013 | Rigatti | C12Q 1/6837 506/30 |
| 2014/0051585 A1 | 2/2014 | Prosen et al. | |
| 2016/0102343 A1* | 4/2016 | Filen | C12Q 1/689 435/6.12 |
| 2016/0289747 A1 | 10/2016 | Eboigbodin et al. | |

FOREIGN PATENT DOCUMENTS

| | | |
|---|---|---|
| EP | 1598427 A1 | 11/2005 |
| EP | 1634963 A1 | 3/2006 |
| WO | 1999055914 A1 | 11/1999 |
| WO | 2001020035 A2 | 3/2001 |
| WO | 2003072805 A2 | 9/2003 |
| WO | 2006051988 A1 | 5/2006 |
| WO | 2007096702 A2 | 8/2007 |
| WO | 2008015396 A2 | 2/2008 |
| WO | 2008035205 A2 | 3/2008 |
| WO | 2009150467 A1 | 12/2009 |
| WO | 2014173963 A1 | 10/2014 |
| WO | WO2014173963 * | 10/2014 ............... C12Q 1/68 |
| WO | 2015/185655 A1 | 12/2015 |

OTHER PUBLICATIONS

Knapp M, Stiller M, Meyer M. Generating barcoded libraries for multiplex high-throughput sequencing. Methods Mol Biol. 2012; 840:155-70. (Year: 2012).*
Bentley et al. Accurate whole human genome sequencing using reversible terminator chemistry. Nature. Nov. 6, 2008; 456(7218):53-9. (Year: 2008).*
Allawi HT, Li H, Sander T, Aslanukov A, Lyamichev VI, Blackman A, Elagin S, Tang YW. Invader plus method detects herpes simplex virus in cerebrospinal fluid and simultaneously differentiates types 1 and 2. J Clin Microbiol. Sep. 2006; 44(9):3443-7. (Year: 2006).*
Margulies et al. Genome sequencing in microfabricated high-density picolitre reactors. Nature. Sep. 15, 2005; 437(7057):376-80. Epub Jul. 31, 2005. (Year: 2005).*
Marguiles et al. (2005, Supplementary Methods pp. 1-34, Nature 437(7057):376-80). (Year: 2005).*
Gansauge MT, Meyer M. Single-stranded DNA library preparation for thesequencing of ancient or damaged DNA. Nat Protoc. Apr. 2013; 8(4)737-48. Epub Mar. 14, 2013. (Year: 2013).*
White RA 3rd, Blainey PC, Fan HC, Quake SR. Digital PCR provides sensitive and absolute calibration for high throughput sequencing. BMC Genomics. Mar. 19, 2009; 10:116. (Year: 2009).*
Demidov, Vadim "PD-loop technology: PNA openers at work" Expert Rev. Mol. Diagn. 1(3), 343-351 (2001).
Demidov & Frank-Kamenetskii "PNA Openers and Their Applications" Methods in Molecular Biology, vol. 208: Peptide Nucleic Acids: Methods and Protocols, 2002, pp. 119-130.

(Continued)

*Primary Examiner* — Teresa E Strzelecka
*Assistant Examiner* — Olayinka A Oyeyemi
(74) *Attorney, Agent, or Firm* — Norton Rose Fulbright US LLP

(57) ABSTRACT

Methods for amplification of a target nucleic acid sequence comprising strand invasion are provided in which strand invasion occurs both at upstream and downstream regions of the target nucleic acid sequence. Further provided are kits and compositions suitable for use in such methods. The methods may comprise amplifying a target nucleic acid sequence comprising a region of unknown sequence, or determining the sequence of a target nucleic acid comprising a region of unknown sequence.

14 Claims, 16 Drawing Sheets
Specification includes a Sequence Listing.

(56) References Cited

OTHER PUBLICATIONS

Didenko, Vladimir V. "DNA probes using fluorescence resonance energy transfer (FRET): designs and applications" Biotechniques, Nov. 2001, 31(5): 1106-1121.

Gill et al: "Nucleic acid isothermal amplification technologies—A review," Nucleosides, Nucleotides and Nucleic Acids, Taylor & Francis, Philadelphia, PA, vol. 27, No. 3, Mar. 1, 2008, pp. 224-243.

Hoser et al. "Strand Invasion Based Amplification (SIBA): A Novel Isothermal DNA Amplification Technology Demonstrating High Specificity and Sensitivity for a Single Molecule of Target Analyte" PLOS One Nov. 2014.

Lavery et al. "Enhancement of recA Protein-promoted DNA Strand Exchange Activity by Volume-occupying Agents" J. Biol. Chern., May 5, 1992, vol. 267, No. 13, pp. 9307-9314.

Lee et al. "Detection of genetically modified organisms (GMOs) using isothermal amplification of target DNA sequences." (2009) BMC Biotechnology 9: 7.

Marras, Salvatore AE "Selection of Fluorophore and Quencher Pairs for Fluorescent Nucleic Acid Hybridization Probes" Public Health Research Institute, Interactive Fluorescent Energy Transfer Nucleic Acid Probes, Edited by Didenko V, vol. 335: Humana Press; 2006: 3-16.

Mori et al: "Loop-mediated isothermal amplification (LAMP): a rapid, accurate, and cost-effective diagnostic method for infectious diseases," Journal of Infection and Chemotherapy, vol. 15, No. 2, Apr. 2009, pp. 62-69.

Piepenburg Olaf et al., "DNA detection using recombination proteins" PLOS Biology Public Library of Science, US, vol. 4, No. 7, Jul. 1, 2006.

Reynisson et al. "Evaluation of probe chemistries and platforms to improve the detection limit of real-time PCR", Journal of Microbiological Methods, Elsevier, Amsterdam, NL, vol. 66, No. 2, Aug. 1, 2006.

Smulevitch et al., "Enhancement of strand invasion by oligonucleotides through manipulation of backbone charge" Nature Biotechnology, Nature Publishing Group, US, vol. 14, Dec. 1, 1996 (Dec. 1, 1996), pp. 1700-1704.

Taylor et al. "Isothermal quadruplex priming amplification for DNA-based diagnostics. Biophysical Chemistry" (2013)171: 1-8.

Tong et al. "Multiple strategies to improve sensitivity, speed and robustness of isothermal nucleic acid amplification for rapid pathogen detection." BMC Biotechnology (2011) 11: 50.

Lalande, Valerie, et al; "Evaluation of a Loop-Mediated Isothermal Amplification Assay for Diagnosis fo Clostridium difficile Infections"; Journal of Clinical Microbiology, Jul. 2011, vol. 49, No. 7, p. 2714-2716.

Patrushev, L.I., "Artificial Genetic Systems", Shemyakin-Ovchinnikov Institute of bioorganic chemistry; Part I: "Genetic and Protein Engineering", 2004, pp. 233-237, Nauka (publisher).

English translation of Russian Office Action dated Dec. 2, 2019, issued during examination of Russia Patent Application No. 2016145448/10 (073024).

* cited by examiner

Non-denaturing electrophoresis of the corresponding reaction products. Lane 1, BioRad EZ Load 20 bp Molecular Ruler; lane 2-6 copied $10^7$, $10^6$, $10^5$, $10^4$ and $10^3$ respectively; lane 7, water.

SEQUENCE LISTING

<160> NUMBER OF SEQ ID NOS: 31

<210> SEQ ID NO 1
<211> LENGTH: 61
<212> TYPE: DNA
<213> ORGANISM: Artificial Sequence
<220> FEATURE:
<223> OTHER INFORMATION: INVASION OLIGONUCLEOTIDE
<220> FEATURE:
<221> NAME/KEY: misc_feature
<222> LOCATION: (48)..(60)
<223> OTHER INFORMATION: 2'-O-METHYL RNA
<220> FEATURE:
<221> NAME/KEY: misc_feature

```
<222> LOCATION: (61)..(61)
<223> OTHER INFORMATION: INVERTED dTTP

<400> SEQUENCE: 1
ttgtccatag actgctcgac ctgatacacg ttatcgtcca tacggatucg ggaucucaua      60
t                                                                      61

<210> SEQ ID NO 2
<211> LENGTH: 57
<212> TYPE: DNA
<213> ORGANISM: Artificial Sequence
<220> FEATURE:
<223> OTHER INFORMATION: INVASION OLIGONUCLEOTIDE
<220> FEATURE:
<221> NAME/KEY: misc_feature
<222> LOCATION: (44)..(56)
<223> OTHER INFORMATION: 2'-O-METHYL RNA
<220> FEATURE:
<221> NAME/KEY: misc_feature
<222> LOCATION: (57)..(57)
<223> OTHER INFORMATION: INVERTED dTTP

<400> SEQUENCE: 2
tcctcctgta cctcgttaca aacaggtgta tttagtacag aagauggauu uaaauat         57

<210> SEQ ID NO 3
<211> LENGTH: 21
<212> TYPE: DNA
<213> ORGANISM: Artificial Sequence
<220> FEATURE:
<223> OTHER INFORMATION: PRIMER

<400> SEQUENCE: 3
aacaagaagg cgtactcgac c                                                21

<210> SEQ ID NO 4
<211> LENGTH: 16
<212> TYPE: DNA
<213> ORGANISM: Artificial Sequence
<220> FEATURE:
<223> OTHER INFORMATION: PRIMER

<400> SEQUENCE: 4
tggggcaaaa tattta                                                      16

<210> SEQ ID NO 5
<211> LENGTH: 21
<212> TYPE: DNA
<213> ORGANISM: Artificial Sequence
<220> FEATURE:
<223> OTHER INFORMATION: PRIMER

<400> SEQUENCE: 5
aaccaaagtg gagtgttaca a                                                21

<210> SEQ ID NO 6
<211> LENGTH: 62
<212> TYPE: DNA
<213> ORGANISM: Artificial Sequence
<220> FEATURE:
<223> OTHER INFORMATION: NON-COMPLEMENTARY INVASION OLIGONUCLEOTIDE
<220> FEATURE:
<221> NAME/KEY: misc_feature
<222> LOCATION: (47)..(61)
<223> OTHER INFORMATION: 2'-O-METHYL RNA
<220> FEATURE:
<221> NAME/KEY: misc_feature
<222> LOCATION: (62)..(62)
```

<223> OTHER INFORMATION: INVERTED dTTP

<400> SEQUENCE: 6
ttgtccatag actgctgaaa aaaccgcatc atttatgata tgcttcuccu cgcauaaucu    60
at                                                                   62

<210> SEQ ID NO 7
<211> LENGTH: 21
<212> TYPE: DNA
<213> ORGANISM: Artificial Sequence
<220> FEATURE:
<223> OTHER INFORMATION: NON-COMPLEMENTARY PRIMER

<400> SEQUENCE: 7
gtgtacagag catttaagat t                                              21

<210> SEQ ID NO 8
<211> LENGTH: 27
<212> TYPE: DNA
<213> ORGANISM: Artificial Sequence
<220> FEATURE:
<223> OTHER INFORMATION: PROBE
<220> FEATURE:
<221> NAME/KEY: misc_feature
<222> LOCATION: (8)..(8)
<223> OTHER INFORMATION: CARBOXYTETRAMETHYLRHODAMINE TAG
<220> FEATURE:
<221> NAME/KEY: misc_feature
<222> LOCATION: (16)..(16)
<223> OTHER INFORMATION: BLACK HOLE QUENCHER 2 TAG
<220> FEATURE:
<221> NAME/KEY: misc_feature
<222> LOCATION: (27)..(27)
<223> OTHER INFORMATION: INVERTED dTTP

<400> SEQUENCE: 8
gtacacatca acugttagct ggggcat                                        27

<210> SEQ ID NO 9
<211> LENGTH: 31
<212> TYPE: DNA
<213> ORGANISM: Artificial Sequence
<220> FEATURE:
<223> OTHER INFORMATION: PROBE
<220> FEATURE:
<221> NAME/KEY: misc_feature
<222> LOCATION: (10)..(10)
<223> OTHER INFORMATION: CARBOXYTETRAMETHYLRHODAMINE TAG
<220> FEATURE:
<221> NAME/KEY: misc_feature
<222> LOCATION: (20)..(20)
<223> OTHER INFORMATION: BLACK HOLE QUENCHER 2 TAG
<220> FEATURE:
<221> NAME/KEY: misc_feature
<222> LOCATION: (29)..(29)
<223> OTHER INFORMATION: INVERTED dTTP
<220> FEATURE:
<221> NAME/KEY: misc_feature
<222> LOCATION: (31)..(31)
<223> OTHER INFORMATION: INVERTED dTTP

<400> SEQUENCE: 9
tgatacacgt tatcguccat acggattcgg t                                   31

<210> SEQ ID NO 10
<211> LENGTH: 14
<212> TYPE: DNA
<213> ORGANISM: Artificial Sequence
<220> FEATURE:
<223> OTHER INFORMATION: PRIMER -continued

<400> SEQUENCE: 10
aacaagaagg cgta                                                14

<210> SEQ ID NO 11
<211> LENGTH: 129
<212> TYPE: DNA
<213> ORGANISM: Artificial Sequence
<220> FEATURE:
<223> OTHER INFORMATION: TARGET TEMPLATE

<400> SEQUENCE: 11
aacaagaagg cgtactcgac ctgatacacg ttatcgtcca tacggattcg ggatctcagt     60
acacatcaac tggttacaaa caggtgtatt tagtacagaa gatggattta aatattttgc    120
cccagctaa                                                           129

<210> SEQ ID NO 12
<211> LENGTH: 143
<212> TYPE: DNA
<213> ORGANISM: Artificial Sequence
<220> FEATURE:
<223> OTHER INFORMATION: TARGET TEMPLATE

<400> SEQUENCE: 12
aacaagaagg cgtactcgac ctgatacacg ttatcgtcca tacggattcg ggatctcagt     60
acacatcaac tgttagctgg ggcaaaatat ttaaatccat cttctgtact aaatacacct    120
gtttgtaaca ctccactttg gtt                                           143

<210> SEQ ID NO 13
<211> LENGTH: 60
<212> TYPE: DNA
<213> ORGANISM: Artificial Sequence
<220> FEATURE:
<223> OTHER INFORMATION: INVASION OLIGONUCLEOTIDE
<220> FEATURE:
<221> NAME/KEY: misc_feature
<222> LOCATION: (45)..(59)
<223> OTHER INFORMATION: 2'-O-METHYL RNA
<220> FEATURE:
<221> NAME/KEY: misc_feature
<222> LOCATION: (60)..(60)
<223> OTHER INFORMATION: INVERTED dTTP

<400> SEQUENCE: 13
ttgtccatag acacgcaaat gaaagacgtt cttaacaagt ttcagaaaga uuugauggct     60

<210> SEQ ID NO 14
<211> LENGTH: 20
<212> TYPE: DNA
<213> ORGANISM: Artificial Sequence
<220> FEATURE:
<223> OTHER INFORMATION: PRIMER

<400> SEQUENCE: 14
gctttaaccg aacagcaaat                                               20

<210> SEQ ID NO 15
<211> LENGTH: 19
<212> TYPE: DNA
<213> ORGANISM: Artificial Sequence
<220> FEATURE:
<223> OTHER INFORMATION: PRIMER

<400> SEQUENCE: 15

```
gcagtacgct tagccatca                                                    19
```

```
<210> SEQ ID NO 16
<211> LENGTH: 324
<212> TYPE: DNA
<213> ORGANISM: Artificial Sequence
<220> FEATURE:
<223> OTHER INFORMATION: TARGET TEMPLATE
<220> FEATURE:
<221> NAME/KEY: misc_feature
<222> LOCATION: (5)..(63)
<223> OTHER INFORMATION: ADAPTOR REGION
<220> FEATURE:
<221> NAME/KEY: misc_feature
<222> LOCATION: (264)..(320)
<223> OTHER INFORMATION: ADAPTOR REGION

<400> SEQUENCE: 16
aaaagcttta accgaacagc aaatgaaaga cgttcttaac aagtttcaga aagatttgat      60
ggctgtctgt gcttctgtgg tgccgagcat tagccccagg aactgcacct cctcctgtct    120
cacggggctg atggtgggtc cagcatctag gagagtgtga cacagggtgg ttggtgctct    180
ggcgctgatt tgagttctca gatctctgag accccagcag aggctgcacg gtaccccaaa    240
tccgcacagc cattgacggg atggcaaatg aaagacgttc ttaacaagtt tcagaaagat    300
ttgatggcta agcgtactgc aaaa                                            324
```

```
<210> SEQ ID NO 17
<211> LENGTH: 191
<212> TYPE: DNA
<213> ORGANISM: Artificial Sequence
<220> FEATURE:
<223> OTHER INFORMATION: TARGET TEMPLATE
<220> FEATURE:
<221> NAME/KEY: misc_feature
<222> LOCATION: (5)..(60)
<223> OTHER INFORMATION: ADAPTOR REGION
<220> FEATURE:
<221> NAME/KEY: misc_feature
<222> LOCATION: (136)..(187)
<223> OTHER INFORMATION: ADAPTOR REGION

<400> SEQUENCE: 17
tcagaaccaa agtggagtgt tacaaacagg tgtatttagt acagaagatg gatttaaata      60
acacatacat aacagacctt tatcttatat ccctcggca accctgaagc tgcaatgaat    120
tgatatctgt cgttcgttac aaacaggtgt atttagtaca gaagatggat ttaaatattt    180
tgccccatca g                                                          191
```

```
<210> SEQ ID NO 18
<211> LENGTH: 195
<212> TYPE: DNA
<213> ORGANISM: Artificial Sequence
<220> FEATURE:
<223> OTHER INFORMATION: TARGET TEMPLATE
<220> FEATURE:
<221> NAME/KEY: misc_feature
<222> LOCATION: (5)..(60)
<223> OTHER INFORMATION: ADAPTOR REGION

<400> SEQUENCE: 18
aaaaaaccaa agtggagtgt tacaaacagg tgtatttagt acagaagatg gatttaaata      60
cacccaaggc ctcacactcg atactgtttt gagcgcctct gtcatggttg atatggtcat    120
cagggccaag tggaatattt aaatccatct tctgtactaa atacacctgt ttgtaacact    180
ccactttggt taaaa                                                      195
```

<210> SEQ ID NO 19
<211> LENGTH: 197
<212> TYPE: DNA
<213> ORGANISM: Artificial Sequence
<220> FEATURE:
<223> OTHER INFORMATION: TARGET TEMPLATE

<400> SEQUENCE: 19

```
tcaggcagta cgcttagcca tcaaatcttt ctgaaacttg ttaagaacgt ctttcatttg      60
cccggcaaat tgagtcacgg tcggtaacac tttcagcaaa gtccggattt gaagcgtaac     120
ccgcattaaa agaaatgcaa atgaaagacg ttcttaacaa gtttcagaaa gatttgatgg     180
ctaagcgtac tgctcag                                                    197
```

<210> SEQ ID NO 20
<211> LENGTH: 140
<212> TYPE: DNA
<213> ORGANISM: Artificial Sequence
<220> FEATURE:
<223> OTHER INFORMATION: TARGET TEMPLATE

<400> SEQUENCE: 20

```
aagaaggcgt actcgacctg atacacgtta tcgtccatac ggattcggga tctcagtaca      60
catcaactgt tagctggggc aaaatattta aatccatctt ctgtactaaa tacacctgtt     120
tgtaacactc cactttggtt                                                 140
```

<210> SEQ ID NO 21
<211> LENGTH: 56
<212> TYPE: DNA
<213> ORGANISM: Artificial Sequence
<220> FEATURE:
<223> OTHER INFORMATION: LABELLED INVASION OLIGONUCLEOTIDE
<220> FEATURE:
<221> NAME/KEY: misc_feature
<222> LOCATION: (13)..(13)
<223> OTHER INFORMATION: BLACK HOLE QUENCHER 2 TAG
<220> FEATURE:
<221> NAME/KEY: misc_feature
<222> LOCATION: (44)..(56)
<223> OTHER INFORMATION: 2'-O-METHYL RNA

<400> SEQUENCE: 21

```
tcctcctgta cctcgttaca aacaggtgta tttagtacag aagauggauu uaaaua           56
```

<210> SEQ ID NO 22
<211> LENGTH: 56
<212> TYPE: DNA
<213> ORGANISM: Artificial Sequence
<220> FEATURE:
<223> OTHER INFORMATION: LABELLED INVASION OLIGONUCLEOTIDE
<220> FEATURE:
<221> NAME/KEY: misc_feature
<222> LOCATION: (44)..(56)
<223> OTHER INFORMATION: 2'-O-METHYL RNA
<220> FEATURE:
<221> NAME/KEY: misc_feature
<222> LOCATION: (56)..(56)
<223> OTHER INFORMATION: BLACK HOLE QUENCHER 3 TAG

<400> SEQUENCE: 22

```
tcctcctgta cctcgttaca aacaggtgta tttagtacag aagauggauu uaaaua           56
```

<210> SEQ ID NO 23
<211> LENGTH: 21
<212> TYPE: DNA

```
<213> ORGANISM: Artificial Sequence
<220> FEATURE:
<223> OTHER INFORMATION: LABELLED PRIMER
<220> FEATURE:
<221> NAME/KEY: misc_feature
<222> LOCATION: (14)..(14)
<223> OTHER INFORMATION: 6-CARBOXY-X-RHODAMINE TAG

<400> SEQUENCE: 23
aaccaaagtg gagtgttaca a                                         21

<210> SEQ ID NO 24
<211> LENGTH: 16
<212> TYPE: DNA
<213> ORGANISM: Artificial Sequence
<220> FEATURE:
<223> OTHER INFORMATION: LABELLED PRIMER
<220> FEATURE:
<221> NAME/KEY: misc_feature
<222> LOCATION: (11)..(11)
<223> OTHER INFORMATION: Cy5 TAG

<400> SEQUENCE: 24
tggggcaaaa tattta                                               16

<210> SEQ ID NO 25
<211> LENGTH: 20
<212> TYPE: DNA
<213> ORGANISM: Artificial Sequence
<220> FEATURE:
<223> OTHER INFORMATION: PRIMER

<400> SEQUENCE: 25
agttgatgtg tactgagatc                                           20

<210> SEQ ID NO 26
<211> LENGTH: 151
<212> TYPE: DNA
<213> ORGANISM: Artificial Sequence
<220> FEATURE:
<223> OTHER INFORMATION: TARGET TEMPLATE

<400> SEQUENCE: 26
cagttgatgt gtactgagat cccgaatccg tatggacgat aacgtgtatc aggtcgagaa    60
aagtacacat caactgttag ctggggcaaa aaagcaaatg aaagacgttc ttaacaagtt   120
tcagaaagat ttgatggcta gcgtactgct g                                 151

<210> SEQ ID NO 27
<211> LENGTH: 56
<212> TYPE: DNA
<213> ORGANISM: Artificial Sequence
<220> FEATURE:
<223> OTHER INFORMATION: ADAPTOR

<400> SEQUENCE: 27
aaccaaagtg gagtgttaca acaggtgta tttagtacag aagatggatt taaata         56

<210> SEQ ID NO 28
<211> LENGTH: 59
<212> TYPE: DNA
<213> ORGANISM: Artificial Sequence
<220> FEATURE:
<223> OTHER INFORMATION: ADAPTOR

<400> SEQUENCE: 28
gctttaaccg aacagcaaat gaaagacgtt cttaacaagt ttcagaaaga tttgatggc     59
```

```
<210> SEQ ID NO 29
<211> LENGTH: 57
<212> TYPE: DNA
<213> ORGANISM: Artificial Sequence
<220> FEATURE:
<223> OTHER INFORMATION: ADAPTOR

<400> SEQUENCE: 29
gcagtacgct tagccatcaa atctttctga aacttgttaa gaacgtcttt catttgc      57

<210> SEQ ID NO 30
<211> LENGTH: 56
<212> TYPE: DNA
<213> ORGANISM: Artificial Sequence
<220> FEATURE:
<223> OTHER INFORMATION: ADAPTOR

<400> SEQUENCE: 30
aaccaaagtg gagtgttaca aacaggtgta tttagtacag aagatggatt taaata      56

<210> SEQ ID NO 31
<211> LENGTH: 52
<212> TYPE: DNA
<213> ORGANISM: Artificial Sequence
<220> FEATURE:
<223> OTHER INFORMATION: ADAPTOR

<400> SEQUENCE: 31
tggggcaaaa tatttaaatc catcttctgt actaaataca cctgtttgta ac      52
```

STRAND-INVASION BASED DNA AMPLIFICATION METHOD

CROSS REFERENCE TO RELATED APPLICATIONS

This application is a national phase application under 35 U.S.C. § 371 that claims priority to International Application No. PCT/EP2015/062430 filed Jun. 3, 2015, which claims priority to Great Britain Patent Application No. 1410022.6, Jun. 5, 2014, all of which are incorporated herein by reference in their entirety.

FIELD OF THE INVENTION

The invention relates to methods of amplification of a target nucleic acid sequence comprising strand invasion. The invention further relates to kits and compositions suitable for use in such methods.

BACKGROUND TO THE INVENTION

Methods for amplification of a target nucleic acid sequence by strand invasion have been described for example in WO2009/150467. Invasion of the target nucleic acid sequence is mediated by a single strand invasion oligonucleotide, which opens up a target duplex to allow binding of both upstream and downstream primers.

BRIEF DESCRIPTION OF THE SEQUENCES

Figure 1:
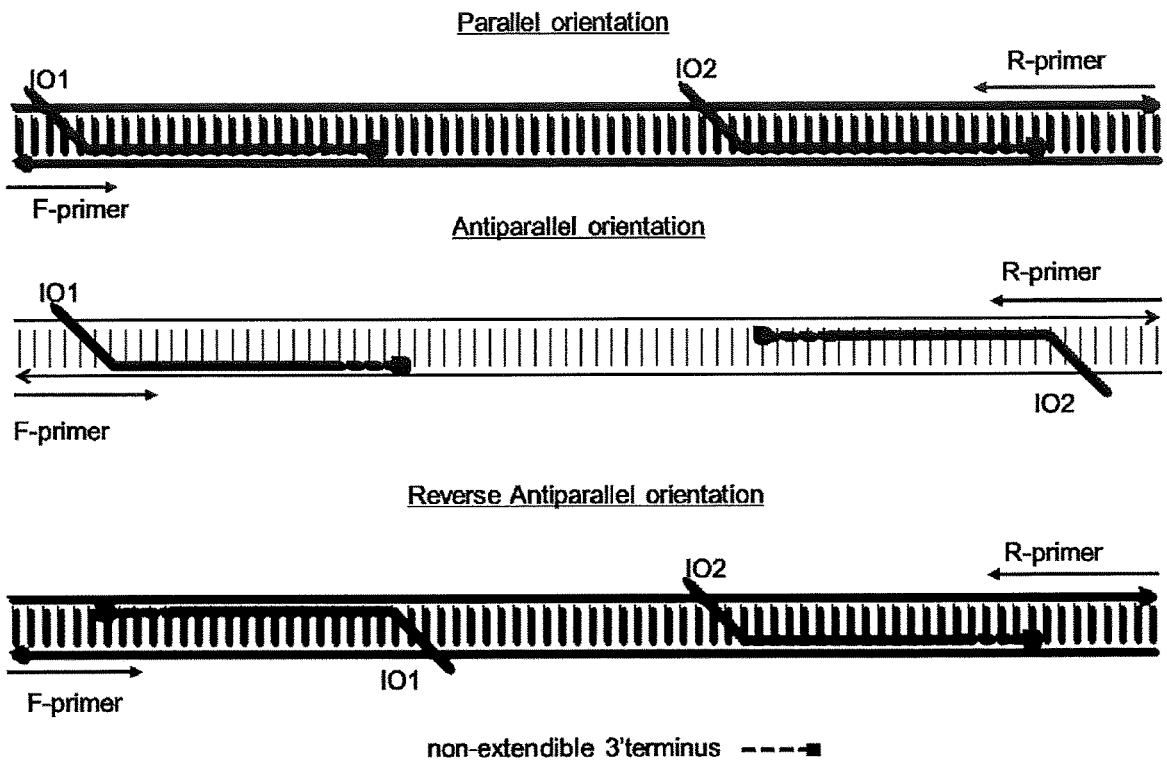
FIG. 1: Amplification of a target DNA using two invasion oligonucleotides with either parallel invasion oligonucleotide configuration, anti-parallel invasion oligonucleotide configuration or reverse anti-parallel configuration. IO1—first strand invasion oligonucleotide; IO2—second strand invasion oligonucleotide. F-primer—forward or upstream primer; R-primer—reverse or downstream primer. The non-extendible terminus of IO1 and IO2 is shown as a dashed line.

SEQ ID NO: 1 is the nucleotide sequence of an invasion oligonucleotide.
SEQ ID NO: 2 is the nucleotide sequence of an invasion oligonucleotide.
SEQ ID NO: 3 is the nucleotide sequence of a DNA primer.
SEQ ID NO: 4 is the nucleotide sequence of a DNA primer.
SEQ ID NO: 5 is the nucleotide sequence of a DNA primer.
SEQ ID NO: 6 is the nucleotide sequence of a non-complementary invasion oligonucleotide.
SEQ ID NO: 7 is the nucleotide sequence of a non-complementary DNA primer.
SEQ ID NO: 8 is the nucleotide sequence of a probe.
SEQ ID NO: 9 is the nucleotide sequence of a probe.
SEQ ID NO: 10 is the nucleotide sequence of a DNA primer.
SEQ ID NO: 11 is the nucleotide sequence of a target template.
SEQ ID NO: 12 is the nucleotide sequence of a target template.
SEQ ID NO: 13 is the nucleotide sequence of an invasion oligonucleotide.
SEQ ID NO: 14 is the nucleotide sequence of a DNA primer.
SEQ ID NO: 15 is the nucleotide sequence of a DNA primer.
SEQ ID NO: 16 is the nucleotide sequence of a target template.
SEQ ID NO: 17 is the nucleotide sequence of a target template.
SEQ ID NO: 18 is the nucleotide sequence of a target template.
SEQ ID NO: 19 is the nucleotide sequence of a target template.
SEQ ID NO: 20 is the nucleotide sequence of a target template.
SEQ ID NO: 21 is the nucleotide sequence of a labelled invasion oligonucleotide.
SEQ ID NO: 22 is the nucleotide sequence of a labelled invasion oligonucleotide.
SEQ ID NO: 23 is the nucleotide sequence of a labelled primer.
SEQ ID NO: 24 is the nucleotide sequence of a labelled primer.
SEQ ID NO: 25 is the nucleotide sequence of a DNA primer.
SEQ ID NO: 26 is the nucleotide sequence of a target template.
SEQ ID NO: 27 is the nucleotide sequence of an adaptor.
SEQ ID NO: 28 is the nucleotide sequence of an adaptor.
SEQ ID NO: 29 is the nucleotide sequence of an adaptor.
SEQ ID NO: 30 is the nucleotide sequence of an adaptor.
SEQ ID NO: 31 is the nucleotide sequence of an adaptor.

SUMMARY OF THE INVENTION

The present invention relates to a system for strand invasion of a target nucleic acid sequence at at least two locations. The methods of the invention use one or more strand invasion oligonucleotides to bind and invade upstream and downstream regions of the target nucleic acid sequence, allowing binding of upstream and downstream primers to effect amplification of the target nucleic acid sequence. Providing for strand invasion of a target nucleic acid sequence at both an upstream and a downstream location couples each primer binding event to an independent strand invasion event and provides increased possibilities for use of strand invasion oligonucleotide sequences that do not have overlap with amplification primers. Strand invasion mediated at two different locations also provides advantages for amplification of target nucleic acid sequences that are longer than those that can typically be amplified from a single point of strand invasion.

Additionally, the same strand invasion species can invade both at an upstream and downstream location provided suitable binding sequences are present in both regions of the target sequence. Similarly, a single primer species may be used where a suitable binding sequence is present in both regions of the target sequence. These embodiments permit amplification and sequencing of unknown sequences where known binding regions (such as adaptor sequences) are present in a template comprising the target sequence. Strand invasion oligonucleotides may also be designed to bind to upstream and downstream binding regions of a duplex target nucleic acid sequence in alternative configurations. This provides opportunities to vary design of sequences for targeting a particular amplicon to optimise amplification parameters. Furthermore, strand invasion oliognucleotides and primers may be designed to have non-overlapping binding regions such that a region of the amplicon remains free for binding of a probe, thus reducing competition between oligonucleotide species for binding the amplicon during amplification and avoiding detection of non-specific amplification products.

Accordingly, the present invention provides a method for amplification of a target nucleic acid sequence, said method comprising contacting said target nucleic acid sequence with at least one upstream primer, at least one downstream primer and first and second strand invasion oligonucleotides under conditions promoting amplification of said target nucleic acid sequence, wherein the first strand invasion oligonucleotide renders an upstream binding region of the target nucleic acid sequence single-stranded to allow the binding of the upstream primer, and the second strand invasion oligonucleotide renders a downstream binding region of the target nucleic acid sequence single-stranded to allow the binding of the downstream primer.

The invention further provides a method for amplification of a target nucleic sequence comprising upstream and downstream binding regions for a strand invasion oligonucleotide, comprising contacting said target nucleic acid sequence with a strand invasion oligonucleotide and one or more primers capable of amplifying the target nucleic acid sequence, wherein the strand invasion oligonucleotide renders the upstream and downstream strand invasion oligonucleotide binding regions of the target nucleic acid sequence single-stranded to allow the binding of said one or more primers.

The invention also provides a kit comprising at least one upstream and at least one downstream primer for a target nucleic acid sequence, and first and second strand invasion oligonucleotides which respectively have upstream and downstream binding regions in a target nucleic acid sequence.

The invention further provides a kit comprising a strand invasion oligonucleotide and one or more primers, and at least one DNA adaptor, wherein said strand invasion oligonucleotide can bind the DNA adaptor when present in an upstream binding region and a downstream binding region of a target nucleic acid sequence, and wherein said one or more primers are capable of amplifying said target nucleic acid sequence.

The invention additionally provides a method of amplifying a target nucleic acid sequence comprising a region of unknown sequence comprising creating a target nucleic acid sequence comprising strand invasion oligonucleotide binding regions upstream and downstream of said region of unknown sequence, and carrying out a method of the invention employing strand invasion oligonucleotides and primers to amplify the target nucleic acid sequence.

The invention further provides a method of determining the sequence of a target nucleic acid comprising a region of unknown sequence, comprising creating a target nucleic acid sequence comprising strand invasion oligonucleotide binding regions upstream and downstream of said region of unknown sequence, carrying out a method of the invention employing strand invasion oligonucleotides and primers to amplify the target nucleic acid sequence, and determining the sequence of said region of unknown sequence.

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting. In addition as used in this specification and the appended claims, the singular forms "a", "an", and "the" include plural referents unless the content clearly dictates otherwise. Thus, for example, reference to "a polypeptide" includes two or more such polypeptides, and the like. All publications, patents and patent applications cited herein, whether supra or infra, are hereby incorporated by reference in their entirety.

Methods for Amplification of a Target Nucleic Acid Sequence

The methods of the invention provide for amplification of a target nucleic acid sequence by strand invasion of a nucleic acid at two separate sites. Strand invasion at each site, mediated by a strand invasion oligonucleotide, renders the target nucleic acid sequence single-stranded to allow for binding for a primer. The primers are typically not able to amplify the target nucleic acid sequence when contacted thereto in the absence of the strand invasion oligonucleotide(s). In other words, the primers are not able to bind to their binding regions in the target nucleic acid sequence unless their binding regions are exposed by strand invasion oligonucleotides which render their binding regions single-stranded. The strand invasion oligonucleotides are also typically not capable of extension by a DNA polymerase. In particular, the methods of the invention preferably amplify a target nucleic acid sequence under isothermal conditions in which a target nucleic acid sequence is present in a nucleic acid duplex. Strand invasion at at least two sites of the duplex renders the target nucleic acid sequence single-stranded under isothermal conditions, permitting primer-based amplification.

Target Nucleic Acid Sequence

The target nucleic acid sequence may be of any origin and may for example be artificial or naturally occurring. The target nucleic acid sequence may comprise a known sequence or regions of known and unknown sequence. The target nucleic acid sequence may be human, mammalian, bacterial or viral. The target nucleic acid sequence may be a region of a gene or chromosome. The target nucleic acid sequence may be specific for a genotype or an organism (such as a pathogen) to be detected by DNA amplification. The target nucleic acid sequence may be unique to the genome of a particular species. Thus, the target nucleic acid sequence for detecting a particular species will typically differ from any homologous nucleic acid sequence in a related species. Typically, the target nucleic acid sequence will comprise several mismatches with a homologous nucleic acid sequence in a related species. The target nucleic acid sequence may be a sequence specific to a particular strain of bacteria or a particular serotype, isolate or clade of a virus.

The target nucleic acid sequence to be detected may be of any size and have any sequence. The target nucleic acid sequence or amplicon is of a sufficient length to provide for hybridisation of the upstream and downstream primers and binding of strand invasion oligonucleotide(s) in a suitable manner to upstream and downstream portions of the target sequence. The amplicon is typically at least 60 nucleotides in length, more preferably at least 65, or at least 70 nucleotides in length as measured from the 5' site of binding of the upstream primer to the 5' site of binding of the downstream primer. The amplicon may be about 60 to about 80 nucleotides in length. In some embodiments, the amplicon may be greater than 80, such as greater than 100 nucleotides in length, such as greater than 150, 200, 300, 400, 500, 1000 or more nucleotides in length. The amplicon may be from about 70 to about 1000 nucleotides in length, such as from about 70 to about 800, about 70 to about 600, about 70 to about 500 nucleotides in length, about 70 to about 400, about 100 to about 400, or about 100 to about 200 nucleotides in length.

Examples of suitable target nucleic acid sequences for methods of the invention include SEQ ID NOs 11, 12, 16, 17, 18, 19, 20 and 26.

The target nucleic acid sequence comprises upstream (5') and downstream (3') regions which each include binding regions for a strand invasion oligonucleotide and a primer. The upstream binding regions for a strand invasion oligonucleotide and primer may overlap in sequence or be non-overlapping. Similarly, the downstream binding regions for a strand invasion oligonucleotide and primer may overlap in sequence or be non-overlapping. The target nucleic acid sequence may also comprise binding regions for one or more oligonucleotide probes. The binding regions for a probe may overlap in sequence with the upstream or downstream binding regions for a strand invasion oligonucleotide and/or primer or be non-overlapping with a binding region for any strand invasion oligonucleotide or primer. The binding region for a probe may preferably be located in between the upstream and downstream strand invasion oligonucleotide binding regions of the target nucleic acid sequence. Selection of binding regions for strand invasion oligonucleotides, primers and probes, and design of appropriate sequences for these is discussed in more detail below.

The lengths of the binding regions for the strand invasion oligonucleotides, primers and probes are defined by the lengths of complementary sequences to the target that are included therein, as described below in more detail. As described below, a strand invasion oligonucleotide typically includes at least 25 nucleotides of complementary sequence to the target, and a primer at least 10. Thus each strand invasion oligonucleotide binding region of the target sequence may be at least 25 nucleotides in length and each primer binding region at least 10 nucleotides in length. The target sequence may further comprise a probe binding region of typically at least 10 nucleotides in length.

The upstream and downstream strand invasion oligonucleotide binding regions may be present in the same strand of the target nucleic acid sequence, or may be located in opposing strands of a duplex comprising the target nucleic acid sequence. The strand invasion oligonucleotide(s) may thus bind the target nucleic acid sequence in a parallel orientation on the same strand, aligning 5' to 3' in the same direction. Alternatively, the strand invasion oligonucleotide(s) may bind opposing strands of the target nucleic acid sequence in an antiparallel orientation, aligning 5' to 3' in opposing directions on the target duplex. In an antiparallel orientation, the 3' terminus of each strand invasion oligonucleotide may be directed towards or away from each other. Thus, the 3' termini of each strand invasion oligonucleotide may face towards the centre of the amplicon (antiparallel configuration) or towards its respective amplicon end (reverse anti-parallel configuration). The 3' terminus or the 5' terminus of a strand invasion oligonucleotide may bind proximal to the binding region for a respective primer. The above binding configurations are shown in FIG. 1.

The use of particular binding configurations can provide alternative effects on amplification parameters. For example, where a strand invasion oligonucleotide binds with its 5' end located proximal to the binding region for a respective primer, the binding of the primer may have a different specificity and kinetic profile as compared to a primer binding proximal to the 3' end of a strand invasion oligonucleotide. The 3' terminus of a strand invasion oligonucleotide typically comprises a number of modified nucleotides (such as 2'-O-methyl RNA nucleotides) which may influence binding interactions of a primer binding proximally thereto. In the parallel and reverse antiparallel configurations, it is also considered that specificity of amplification may be enhanced since branch migration of the 3' termini of the strand invasion oligonucleotides (which typically comprise modified nucleotides) is required before primer binding is possible. Accordingly, the methods of the invention provide for variation of amplification rate and specificity of amplification by variation of binding configurations of the strand invasion oligonucleotide(s).

The upstream and downstream strand invasion oligonucleotide binding regions of the target nucleic acid sequence may bind the same species of strand invasion oligonucleotide. Thus, a single species of strand invasion oligonucleotide may be provided to initiate strand invasion at two points in the target nucleic acid sequence, as discussed further below. In this embodiment, the upstream and downstream binding regions each comprise complementary sequence to at least a portion of the strand invasion oligonucleotide. The upstream and downstream binding regions are typically homologous or identical to one another. The upstream and downstream binding regions may be at least 85%, at least 90%, at least 95% homologous or identical to one another or fully identical. The upstream and downstream binding regions may have 1, 2, 3, 4, 5, 6, 7 or 8, such as 1 to 5 or 1 to 3 mismatches between each other. Additionally, a single species of primer may be provided to initiate amplification at two points in the target nucleic acid sequence, as discussed further below. The target nucleic acid sequence will in this case comprise upstream and downstream binding regions which each comprise complementary sequence to at least a portion of the primer, and may be homologous or identical to one another as described above.

More than one target nucleic acid sequence may be detected in a method of the invention by providing multiple combinations of strand invasion oligonucleotide(s), primers (and optionally probes) each specific for a different target nucleic acid sequence. Typically, strand invasion oligonucleotide/primer pairs and/or probes binding to different target nucleic acid sequences will be labeled with different fluorophore/quencher pairs, thus allowing for multiplexing. At least two, three, four, five, ten or more different target sequences may be detected. More than one target nucleic acid sequence from the same organism may be detected. Alternatively, target nucleic acid sequences specific for at least two, three, four, five, ten or more different genotypes, organisms or pathogens may be detected.

Upstream and Downstream Primers

Suitable upstream and downstream primers are selected based on the target nucleic acid sequence of interest, and having regard to the site of binding of the respective strand invasion oligonucleotide that renders an upstream or downstream binding region of the target nucleic acid sequence single-stranded to allow the binding of the respective primer.

The upstream and downstream primers comprise a sequence that is partly or fully complementary to the target and optionally a 5' and/or 3' flanking non-complementary sequence. Alternatively, the upstream and downstream primers may consist entirely of partly or fully complementary sequence to the target. The length of the primer sequence that is complementary to the target is sufficient to provide specific hybridisation to the target nucleic acid sequence. The length of complementary sequence is typically at least 10 nucleotides, more preferably at least 15, at least 16, or at least 17 nucleotides. The length of complementary sequence may be 10-25, 15-25, 10-30 or 15-30 nucleotides.

It should be understood that the above sequence lengths refer to portions of the primers which may be partly or fully complementary to the target nucleic acid sequence. Mismatches may be present between the primers and the target sequence at particular positions while still allowing for specific amplification and detection of the target sequence, in particular having regard to the combined use of upstream and downstream primers and binding of strand invasion oligonucleotide(s) to upstream and downstream regions of the target nucleic acid sequence to achieve amplification. There may be 1, 2, 3, 4 or 5 mismatches between the complementary region of the primer and the corresponding region of the target sequence.

Typically the upstream and downstream primer will be less than 30 nucleotides in total in length, more preferably less than 25 nucleotides in length, such as 15 to 25, or 15 to 23 nucleotides in length. It is particularly preferred that primers of less than 30 nucleotides in length are used where a recombinase is used for strand invasion. Such primers are not capable of acting as substrates for recombinases. In some embodiments primers of less than 15 nucleotides in length may be used, such as primers of about 8 to about 14, about 10 to about 14 or about 12 to about 14 nucleotides in length. The use of such short primers is preferred in combination with a probe having a binding region in the target nucleic acid sequence that does not overlap with the binding region for a primer or strand invasion oligonucleotide. Detection of non-specific amplification products produced by short primers can be reduced or eliminated by using a probe with a non-overlapping binding site.

The upstream (or forward) primer binds to the 3' region of one strand of the duplex target nucleic acid sequence, at a position proximal or overlapping with the binding site of the strand invasion oligonucleotide. The downstream (or reverse) primer binds to the 3' region of the opposing strand of the duplex target nucleic acid sequence to the upstream primer, at a position proximal or overlapping with the binding site of the strand invasion oligonucleotide. The 5' binding sites of the upstream and downstream primers are typically at least 60 nucleotides apart, more preferably at least 65, or at least 70 nucleotides in length on the duplex target sequence.

Depending on the binding configuration of the strand invasion oligonucleotide, as shown in FIG. 1, the upstream primer may have a region of sequence overlap or a region of complementarity with the sequence of the respective strand invasion oligonucleotide. The region of sequence overlap or complementarity may be 1-8 nucleotides in length, and may be at least 5 or at least 6 nucleotides in length. The downstream primer may likewise have a region of sequence overlap or a region of sequence complementarity of 1-8 nucleotides, such as at least 5 or at least 6 nucleotides in length with the sequence of the respective strand invasion oligonucleotide.

Alternatively, there may be no sequence overlap or complementarity between the upstream primer and the respective strand invasion oligonucleotide, and/or no sequence overlap or complementarity between the downstream primer and the respective strand invasion oligonucleotide, with the relevant primer binding instead at a position that is proximal in the target sequence to the binding site of the strand invasion oligonucleotide.

The use of one or more primers that have binding regions in the target that do not overlap with binding regions for strand invasion oligonucleotides can provide various advantages. In embodiments where the methods of the invention utilise oligonucleotide probes to detect DNA amplification, there may also be no sequence overlap or complementarity between a strand invasion oligonucleotide and the probe and/or an upstream and/or downstream primer and the probe. There may be no sequence overlap between the binding regions within the target nucleic acid sequence for the upstream primer, the downstream primer, each strand invasion oligonucleotide, and of any probe. There may also be no complementarity between any of the primers, strand invasion oligonucleotides or probes. Design of sequences for the various oligonucleotide species such that they can bind the target nucleic acid sequence at independent, non-overlapping regions in the target may provide for reduced competition between the oligonucleotide species for binding to the target nucleic acid sequence, and also reduce formation and/or avoid detection of undesired amplification products.

In more detail, primers of between 16 and 23 bases in length are typically used in strand invasion based amplification methods using a single strand invasion oligonucleotide (SIBA methods). The sequences at the 3' ends of the primers have usually about 8 bases overlap or complementarity with the strand invasion oligonucleotide (the upstream primer overlaps the strand invasion oligonucleotide while the downstream primer is complementary to the strand invasion oligonucleotide). This configuration ensures efficient amplification of the target DNA and minimizes the risk of non-specific amplification. It is also possible to use short primers ≤14 bases in length, which do not overlap with the strand invasion oligonucleotide. Short primers which do not have sequences that overlap with the strand invasion oligonucleotide are able to amplify the target DNA more efficiently than long overlapping primers. This is because the 3' end of a longer overlapping primer competes with the strand invasion oligonucleotide for a binding site of the target template. For example, the upstream primer needs to first branch migrate onto the duplex before displacing the strand invasion oligonucleotide.

However, short primers (≤14 bases) can generate non-specific amplification products. To avoid this problem, longer primers (16-23 bases) with 3' ends that overlap or are complementary with the strand invasion oligonucleotide are typically used in SIBA. In this configuration, the region peripheral to the strand invasion oligonucleotide is still around 14 bases long. This leaves only a short peripheral region that dissociates when the target DNA is amplified.

In the methods of the invention comprising strand invasion at two points in the target (upstream and downstream), shorter primers can be used than in SIBA. Furthermore, non-overlapping primers can be used more efficiently. This is because it is possible to incorporate a probe binding site on the target DNA that is independent of the strand invasion oligonucleotides and primers. Furthermore, the ability to use different primer and strand invasion oligonucleotide configurations such as the reverse anti-parallel configuration in the methods of the invention minimize or abolish the risk of short primer-induced non-specific amplification.

Where a primer binds proximal to its respective strand invasion oligonucleotide (without sequence overlap or complementarity), typically there is 15 nucleotides or less, preferably 10 nucleotides or less, such as about 1 to about 15 nucleotides, about 5 to about 15 nucleotides, about 5 to about 10 nucleotides, or about 3 to about 8 nucleotides between the closest boundary of the binding region of the strand invasion oligonucleotide and the binding region of the respective primer. This ensures that the primer is able to hybridise to the single-stranded region created by binding of the strand invasion oligonucleotide.

Preferably, each primer is designed to allow for specific detection of a particular target nucleic acid sequence, such as a particular genotype, or a nucleic acid sequence present in a particular target, such as a particular organism or a particular pathogen. Thus, each primer typically specifically or selectively hybridises to a complementary sequence found only in the target. However, each primer may also hybridise to other sequences, such as sequences found in other species, provided that when used in combination with the second primer, strand invasion oligonucleotide(s) and optional oligonucleotide probe, specific detection of the target nucleic acid sequence is obtained.

Any upstream or downstream primer used in the invention may comprise one or more modified nucleotides and/or a detectable label, for example a fluorescent dye. In some embodiments an upstream or downstream primer may form a FRET pair with a respective strand invasion oligonucleotide, and thus comprise a fluorophore or quencher, as discussed below.

It should be understood that the methods of the invention may comprise use of more than one pair of upstream and downstream primers, typically where more than one target sequence is to be detected in parallel in a multiplex system.

Strand Invasion Oligonucleotide(s)

One or more suitable strand invasion oligonucleotides are selected based on the target nucleic acid sequence of interest, and having regard to the site of binding of the upstream and downstream primers and the requirement for the strand invasion oligonucleotide(s) to render the target nucleic acid sequence single-stranded in the relevant regions to allow for the binding of the upstream primer and downstream primer. Where the target nucleic acid sequence comprises homologous or identical upstream and downstream strand invasion oligonucleotide binding regions, a single species of strand invasion oligonucleotide may be provided to effect amplification. Alternatively, two separate species of strand invasion oligonucleotides (first and second) binding divergent sequences in the upstream and downstream portions of the target nucleic acid sequence may be provided. The following description of the features of a strand invasion oligonucleotide is applicable to both first and second strand invasion oligonucleotides when these are used.

Each strand invasion oligonucleotide comprises a sequence that is complementary to the target and optionally additional flanking non-complementary sequence(s). The length of the sequence that is complementary to the target may be determined by the skilled person empirically and is sufficient to provide for efficient strand invasion of the target nucleic acid sequence, optionally under isothermal conditions. The complementary sequence may comprise RNA-DNA complementary base pairing and modified nucleotides. Typically, the length of complementary sequence is at least 25 or at least 27 nucleotides, typically at least 30 nucleotides, such as least 32, at least 33 or at least 35 nucleotides, more preferably at least 36, 37, 38, 39 or 40 nucleotides in length or greater. The length of complementary sequence may be 30-50, 32-50, 35-50, 40-50, 35 to 48, 35 to 46, 38 to 45 or 40 to 45 nucleotides in length.

It should be understood that the above sequence lengths refer to a portion of a strand invasion oligonucleotide which may be partly or fully complementary to the target nucleic acid sequence. Mismatches may be present between the strand invasion oligonucleotide and the target sequence at particular positions while still allowing for specific amplification and detection of the target sequence, in particular having regard to the combined use of upstream and downstream primers and a strand invasion oligonucleotide to achieve amplification. There may be 1, 2, 3, 4, 5, 6, 7, or 8, such as 1 to 5 or 1 to 3 mismatches between the complementary region of the strand invasion oligonucleotide and the corresponding region of the target sequence, depending on the total length of complementary sequence.

The complementary sequence of a strand invasion oligonucleotide hybridises to a portion of the target sequence which may or may not overlap with a portion of the target sequence forming a binding region for a primer. The strand invasion oligonucleotide may have a region of overlap or complementarity of 1-8 nucleotides, such as a region of at least 5 or at least 6 nucleotides in length, with a respective upstream or downstream primer. Alternatively, the sequence of a strand invasion oligonucleotide may have no region of overlap with the sequence of an upstream or downstream primer. In this embodiment, as discussed above, a strand invasion oligonucleotide will bind at a position proximal to the binding region for an upstream or downstream primer, such that it can render the binding region for the primer single-stranded.

The closest boundaries of the upstream and downstream strand invasion oligonucleotide binding regions of the target nucleic acid sequence may be located at least 15, such as at least 20 or at least 25 nucleotides apart in the target nucleic acid sequence, but shorter distances between the binding regions may also be used in some embodiments.

The 5' portion of the complementary sequence of a strand invasion oligonucleotide typically binds within 25 nucleotides or less, more preferably 20 nucleotides or less from the relevant boundary of the duplex target nucleotide sequence to be melted (the amplicon).

A strand invasion oligonucleotide optionally further comprises non-complementary sequence region(s) to the target that flank the complementary sequence region. A strand invasion oligonucleotide may comprise a non-complementary 5' region which may be of any nucleotide sequence. The 5' non-complementary region is typically at least 3 nucleotides in length, more typically at least 6, at least 8, preferably at least 10, at least 12 or at least 14 nucleotides in length. The 5' non-complementary region may assist binding of recombinase, since recombinase binds cooperatively. A strand invasion oligonucleotide may comprise a 3' non-complementary region typically of 1-3 nucleotides in length which comprises nucleotides which block polymerase extension, such as 3'-prime inverted dT.

A strand invasion oligonucleotide is typically at least 30 nucleotides in length where a recombinase is used for strand invasion in the amplification method in conjunction with the strand invasion oligonucleotide. A strand invasion oligonucleotide is preferably at least 35, at least 40 or at least 45 nucleotides in length, more preferably at least 50, and may be at least 55 nucleotides in length or greater. The strand invasion oligonucleotide may be 40-70, 45-70, 45-70, 50-70, 55-70, 45-65, 50-65, 50-60 or 55-65 nucleotides in length.

Typically a strand invasion oligonucleotide has a non-extendible 3' terminus, such that it cannot serve as a substrate for a DNA polymerase, and the target sequence is then only amplified on the further binding of the specific upstream and downstream primers. This avoids formation of non-specific amplification products. A strand invasion oligonucleotide may comprise one, two, three, four, five, six, seven, eight or more modified nucleotides in its 3' region, such as in the 10-15 or 10-20 nucleotides from the 3' terminus. A strand-invasion oligonucleotide may comprise a 3' modification of the 3' terminal nucleotide, and may be a dideoxynucleotide, or comprise a 3' amino-allyl group, a 3' carbon spacer, 3' phosphate, 3' biotin, 3' sialyl, or 3' thiol. The 3' nucleotide may be a nucleotide incorporated in a reversed orientation by a 3'-3' linkage. Alternatively or additionally, the 3' region of the strand-invasion oligonucleotide may comprise nucleotides with poor substrate capability for DNA polymerases, such as PNA (peptide nucleic acid) nucleotides, LNA (locked nucleic acid), 2'-5' linked DNA, 2'-fluoro RNA or 2'-O-methyl RNA, or combinations thereof.

Where the strand-invasion oligonucleotide is a PNA oligomer comprising, consisting of or consisting essentially of PNA nucleotides, such an oligonucleotide can destabilise and invade duplex DNA in the absence of a recombinase enzyme. Thus, where a PNA oligonucleotide is used, the methods of the invention may be performed without presence of a recombinase enzyme. A PNA oligonucleotide may comprise PNA nucleotides and other nucleotides, such as DNA nucleotides, provided that the oligonucleotide comprises sufficient PNA nucleotides to mediate strand invasion of a duplex. The skilled person can empirically determine the level of PNA to be incorporated into an oligonucleotide by testing its ability to effect strand invasion and allow for DNA amplification.

A strand invasion oligonucleotide may comprise a detectable label, for example a fluorescent dye. In some embodiments a strand invasion oligonucleotide may form a FRET pair with an upstream or downstream primer and thus comprise a fluorophore or quencher, as discussed below.

The methods of the invention comprise strand invasion at at least two sites of a target nucleic acid sequence, mediated by first and second strand invasion oligonucleotides, or by the same species of strand invasion oligonucleotide where the target nucleic acid sequence comprises two binding sites for the same strand invasion oligonucleotide. It should be understood that the methods of the invention may further comprise strand invasion by additional strand invasion oligonucleotides at additional sites of a target nucleic acid sequence, such as at 3 or more, 4 or more, 5 or more, 8 or more, or 10 or more sites. Additionally, in a multiplex system, the methods of the invention may comprise use of additional strand invasion oligonucleotides targeting upstream and downstream binding regions of additional target sequences.

Amplification of the Target Nucleic Acid Sequence

The DNA amplification method comprises strand invasion based amplification. The strand invasion amplification comprises strand invasion at at least two sites in the target nucleic acid sequences. Strand invasion occurs at both upstream and downstream regions of the target nucleic acid sequence.

The target nucleic acid sequence is incubated with the upstream primer, downstream primer, and one or more (such as first and second) strand invasion oligonucleotides capable of rendering both the upstream and downstream binding regions for the respective primers single-stranded, under conditions promoting amplification of said target nucleic acid sequence. In some embodiments, a single species of primer may serve as both the upstream and the downstream primer.

Such conditions typically comprise the presence of a DNA polymerase enzyme. Suitable conditions include any conditions used to provide for activity of polymerase enzymes known in the art. The conditions typically include the presence of dNTPs selected from dATP, dTTP, dCTP, dGTP, dUTP and analogues of any thereof, suitable buffering agents/pH and other factors which are required for enzyme performance or stability. Typically all four of dATP, dTTP, dCTP and dGTP will be present. The conditions may include the presence of detergents and stabilising agents. The temperature used is typically isothermal, i.e. constant throughout the amplification process. The temperature used typically depends on the nature of the polymerase enzyme and other enzyme components, and also reflects the hybridisation temperature required for the primers and strand invasion oligonucleotides.

The polymerase used typically has strand-displacement activity. The term "strand displacement" is used herein to describe the ability of a DNA polymerase, optionally in conjunction with accessory proteins, to displace complementary strands on encountering a region of double stranded DNA during DNA synthesis. Suitable DNA polymerases include polI from *E. coli, B. subtilis*, or *B. stearothermophilus*, and functional fragments or variants thereof, and T4 and T7 DNA polymerases and functional fragments or variants thereof. A preferred polymerase is Bsu DNA polymerase or a functional fragment or variant thereof.

The amplification conditions preferably comprise the presence of a recombinase. Any recombinase system may be used in the method of the invention. The recombinase system may be of prokaryotic or eukaryotic origin, and may be bacterial, yeast, phage, or mammalian. The recombinase may polymerise onto a single-stranded oligonucleotide in the 5'-3' or 3'-5; direction. The recombinase may be derived from a myoviridae phage, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2. In a preferred embodiment, the T4 recombinase UvsX (Accession number: P04529) or a functional variant or fragment thereof is used. The Rad systems of eukaryotes or the recA-Reco system of *E. coli* or other prokaryotic systems may also be used. The recombinase may be *E. coli* RecA.

The conditions may further comprise the presence of recombinase accessory proteins, such as single-stranded binding protein (e.g. T4 gp32, accession number P03695) and recombinase loading agent (e.g. UvsY, accession number NP_049799.2). In a preferred embodiment, the conditions comprise the presence of the T4 gp32, UvsX and UvsY proteins. The recombinase (such as UvsX), and where used the recombinase loading agent (such as UvsY) and single stranded DNA binding protein (such as gp32), can each be native, hybrid or mutant proteins from the same or different myoviridae phage sources. A native protein may be a wild type or natural variant of a protein.

The conditions may further comprise other factors used to enhance the efficiency of the recombinase such as compounds used to control DNA interactions, for example proline, DMSO, BSA, PEG or other crowding agents which are known to enhance loading of recombinases onto DNA (Lavery P. et al. J. Biol. Chem. 1992, 267, (13), 9307-9314).

The conditions may also comprise the presence of an ATP regeneration system. Various ATP regeneration systems are known to the person skilled in the art, and include glycolytic enzymes. Suitable components of an ATP regeneration system may include one or more of phosphocreatine, creatine kinase, myokinase, pyrophosphatase, sucrose and sucrose phosphorylase. The conditions may further comprise the presence of ATP.

Additional components such as magnesium ions, DTT or other reducing agents, salts may also be included.

Further components may include one or more restriction enzymes (such as one or more restriction endonucleases) to digest a nucleic acid comprising a target nucleic acid sequence prior to, or at the same time as contacting the target nucleic acid sequence with other amplification reagents. Amplification rate of a target nucleic acid sequence comprised in DNA plasmid may be increased by digestion of the plasmid with a restriction enzyme, to thus linearise the starting template. Thus, the methods of the invention may comprise contacting a nucleic acid comprising the target nucleic acid to be amplified with a restriction enzyme. Any suitable restriction enzyme having a suitable recognition site in a nucleic acid comprising the target nucleic acid sequence may be used for digestion. The recognition site is typically located in a region of the nucleic acid other than the target nucleic acid sequence.

The various components described above may be provided in varying concentrations to provide for DNA amplification. The skilled person can select suitable working concentrations of the various components in practice.

Detection of Presence of Amplified DNA

The presence of amplified DNA resulting from the contacting of the target nucleic acid sequence with the primers and strand invasion oligonucleotide(s) under conditions promoting DNA amplification may be monitored by any suitable means.

One or both of the primers, or one or more of the strand invasion oligonucleotide(s) (such as the first and/or second strand invasion oligonucleotide(s)) may incorporate a label or other detectable moiety. Any label or detectable moiety may be used. Examples of suitable labels include fluorescent moieties, and FRET pairs of a fluorophore and acceptor moiety. For example, the upstream primer may form a FRET pair with a strand invasion oligonucleotide having an upstream binding region in the target nucleic acid sequence, and/or the downstream primer may form a FRET pair with a strand invasion oligonucleotide having a downstream binding region in the target nucleic acid sequence. The primer(s) may be labelled with a fluorophore or a quencher, with the strand invasion oligonucleotide(s) labelled with the corresponding member of a FRET pair, a quencher or a fluorophore. Suitable labels and attachment sites are described below. The use of such FRET pairs can provide for methods which detect strand invasion and amplification of a target nucleic acid sequence. Other quenching systems detecting changes in interaction of two detectable moieties may also be employed, including contact quenching.

More preferably, or additionally, one or more probes that detect the amplified DNA may be used, again incorporating a label or other detectable moiety. Preferably, the signal from the probe is monitored in real time in conjunction with amplification of the target nucleic acid sequence. A probe may bind at any suitable location in the target nucleic acid sequence. A probe may particularly preferably bind to a region of the target nucleic acid sequence that does not overlap with the binding region for a primer and/or a strand invasion oligonucleotide. Thus, a probe may particularly preferably have a binding site within the target nucleic sequence that is independent from the binding site(s) for one or more other oligonucleotide species. Selection of a non-overlapping binding region for the probe may reduce competition for binding of the probe during amplification. The use of a probe binding at an independent location in the target nucleic acid sequence may also reduce or eliminate detection of non-specific amplification products such as primer-dimers, providing a more accurate detection of amplification of the target nucleic acid sequence.

Probes detecting different amplified target sequences may signal at different fluorescent wavelengths to provide for multiplex detection. Two or more, such as three, four, five, six, eight, ten or more different probes may be used for multiplex detection of several different target sequences in a single reaction. An oligonucleotide probe for use in the methods of the invention is typically about 8 to about 25 nucleotides in length, such as about 10 to about 20, about 12 to about 25, or about 15 to about 25 nucleotides in length. In some embodiments the probe may also function as a strand invasion oligonucleotide (and thus have features described for strand invasion oligonucleotides above). For example, an additional labelled strand invasion oligonucleotide acting as a probe may be provided which has a binding region in the target nucleic acid sequence proximal to the upstream or downstream strand invasion oligonucleotide binding region, such that it can form a FRET pair with the respective strand invasion oligonucleotide binding to the upstream or downstream region. In this embodiment, the strand invasion oligonucleotide binding to the upstream or downstream region may be labelled with a fluorophore or quencher, and the additional strand invasion oligonucleotide labelled with the corresponding interacting detectable moiety (quencher or fluorophore).

The probe may comprise a sequence which is fully complementary in sequence to the target nucleic acid sequence or may have one or more mismatches, such as 2 or 3 mismatches to the target sequence, provided that it is able to specifically detect the target sequence in combination with the strand invasion oligonucleotide(s) and primer(s). An oligonucleotide probe for use in the invention may be a hybridisation probe showing conformational changes on target binding (as described for example in U.S. Pat. No. 7,241,596), a molecular beacon (as described for example in U.S. Pat. No. 5,925,517), or a cleavable probe, such as an endonuclease-cleavable probe (as described for example in U.S. Pat. No. 7,435,561 and US20050214809) or a restriction enzyme-cleavable probe A primer, strand invasion oligonucleotide, or probe used in the methods of the invention may be labeled with any fluorophore or quencher. The fluorophore and quencher will be selected such that the absorption spectrum of the quencher overlaps with the emission spectrum of the fluorophore. The fluorophore and quencher will further be selected and positioned such that, upon hybridization with a target template, the fluorophore produces an increase in signal due to reduced quenching effect.

The quencher may be non-fluorescent, for example a non-fluorescent chromophore. The quencher may be a dark quencher. Alternatively, the quencher may fluoresce with a different emission spectrum to the fluorophore, such that when specifically monitoring fluorescence of the fluorophore or the quencher, a change in either signal may report on hybridisation to the target template. A fluorophore or quencher may be positioned at the 5' or 3' termini of a labelled oligonucleotide species. A 3' terminal location may be useful in particular in embodiments where polymerase-dependent extension is undesirable. A fluorophore or quencher may also be located at an internal position, such as ten or less nucleotides away from the 5' or 3' terminus of the labelled species.

The fluorophore may be any fluorescent moiety, typically a fluorescent organic dye. The quencher may be any moiety which quenches the fluorescence of the fluorophore, and is typically a chromogenic molecule, such as an organic dye. The skilled person is able to select appropriate fluorophore-quencher pairs for an oligonucleotide probe based on their common general knowledge. Suitable pairings are discussed for example in the following references: Marras S E: Selection of Fluorophore and Quencher Pairs for Fluorescent Nucleic Acid Hybridization Probes. In: Fluorescent Energy Transfer Nucleic Acid Probes. Edited by Didenko V, vol. 335: Humana Press; 2006: 3-16, and Didenko V V: DNA probes using fluorescence resonance energy transfer (FRET): designs and applications. Biotechniques 2001, 31(5):1106-1116, 1118, 1120-1101.

Suitable fluorophores include, but are not limited to, fluorescein and fluorescein derivatives, such as carboxyfluoresceins (FAM, including 6-FAM, 5-FAM, dT FAM), VIC, hexachloro-6-carboxyfluorescein (HEX), and JOE, 5-(2'-aminoethyl)aminonaphthalene-1-sulphonic acid (EDANS), coumarin and coumarin derivatives such as 3-phenyl-7-isocyanatocoumarin, Lucifer yellow, NED, Texas red, tetramethylrhodamine, carboxytetramethylrhodamine (TAMRA), 6-carboxy-X-rhodamine (ROX), 5 carboxyrhodamine, N-(p-2-benzoxazolyl)phenyl)maleimide, cyanine dyes such as CY5, rhodamine dyes, xanthene dyes, naphthylamines, acridines, benzoxadiazoles, stilbenes, and pyrenes. Suitable quenchers include, but are not limited to, DABSYL, 4'-(4-dimethylaminophenylazo)benzoic acid (DABCYL), 4-dimethylaminophenylazophenyl-4'-maleimide (DABMI), tetramethylrhodamine, carboxytetramethyl-rhodamine (TAMRA), Black Hole Quencher 1, Black Hole Quencher 2, Black Hole Quencher 3, Dark Quencher 1, Dark Quencher 2, Iowa Black RQ, Iowa Black FQ.

Preferred fluorophore/quencher pairs include:
TAMRA and Black Hole Quencher 2;
ROX and Black Hole Quencher 2;
ROX and DABCYL;
FAM (such as dT-FAM) and Iowa Black FQ;
FAM (such as dT-FAM) and DABCYL;
ROX and Iowa Black FQ;
CY5 and Iowa Black RQ.

The fluorophore or quencher is typically covalently attached to the labelled species of oligonucleotide. The fluorophore or quencher may be attached by any suitable linker to one or more nucleotides present in the sequence of the oligonucleotide species. The skilled person is able to select any appropriate linker based on their common general knowledge. Suitable linkers are discussed for example in Agrawal S (ed.): Protocols for Oligonucleotides and Analogs: Synthesis and Properties: Humana Press; 1993.

In some embodiments, the methods of the invention may comprise use of one or more probes comprising a region complementary to the target nucleic acid sequence, a fluorophore and a quencher. The sequence of such an oligonucleotide probe may comprise at least 20% RNA nucleotides, modified RNA nucleotides and/or PNA nucleotides. The use of such probes has advantages for preventing a fluorescent signal from the probe in the presence of a protein capable of binding to single-stranded DNA (such as a recombinase) in the absence of a complementary template sequence. In other words, at least 20% of the nucleotides present in the oligonucleotide probe are RNA nucleotides, modified RNA nucleotides and/or PNA nucleotides. More preferably, the sequence of the oligonucleotide probe may comprise at least 25%, at least 30%, at least 35%, at least 40%, at least 50%, at least 60%, at least 70%, at least 80%, or at least 90% RNA nucleotides, modified RNA nucleotides and/or PNA nucleotides. Where RNA bases are included in a probe, an RNase H enzyme, such as RNase H2 may be provided in the method of the invention to enhance signal from the probe by cleaving the probe-target duplex and reducing quenching. A preferred RNase H2 enzyme is *Thermococcus gammatolerans* RNase H2. Alternatively, as described above, other forms of cleavable probe may be used, such as restriction enzyme or endonuclease-cleavable probes.

Where a probe labelled with a fluorophore and quencher is used, the fluorophore and quencher are typically positioned at least eight nucleotides apart in the sequence of the probe, more preferably at least ten, or at least twelve nucleotides apart, depending on the length of the probe. The fluorophore and quencher may be located at the 5' and 3' termini, and thus the maximum distance apart that is possible in the probe. The distance between the fluorophore and quencher will be selected such that when the probe is hybridised to the target nucleic acid sequence (in an open or linear conformation) there will be reduced quenching of the fluorophore by the quencher, leading to a detectable signal for the presence of the target nucleic acid sequence. An appropriate distance between the fluorophore and quencher may be optimised empirically.

Dyes which intercalate with amplified DNA may also be used to detect the amplified DNA, such as Sybr green I and thiazole orange.

The detection of the signal from the amplified DNA may be made by any suitable system, including real-time detection methods.

Applications for Amplification Methods

The amplification methods of the invention may be used for any application where specific amplification of a target nucleic acid sequence is desired.

The methods of the invention may be used for detection of a target nucleic acid sequence, and for example for diagnosis of whether a clinical sample contains a target nucleic acid sequence. The present invention is particularly advantageous in the medical setting. The detection methods of the invention provide a highly specific test to allow for determination of presence of a target nucleic acid sequence. The method may be applied to a range of disease settings. The invention provides a method for diagnosis of a disease in a subject, comprising carrying out a method of amplification of a target nucleic acid sequence of the invention in a sample from said subject to detect a target nucleic acid sequence associated with said disease.

Any sample may be used for detection of the target nucleic acid sequence, provided that nucleic acid can be obtained or derived from the sample. The sample may be for instance an environmental sample, a reference sample or a clinical sample. Where the methods of the invention are used for diagnosis of a disease by detection of a target nucleic acid sequence, the sample is commonly a clinical sample, for example a sample obtained from a patient suspected of having, or having the disease. Suitable types of clinical sample vary according to the particular type of disease or infection that is present, or suspected of being present in a subject. The sample may be a saliva, sputum, blood, plasma, serum, urine or stool sample. The sample may be a cell or tissue sample. In preferred embodiments, the samples are taken from animal subjects, such as mammalian subjects. The samples will commonly be taken from human subjects, but the present invention is also applicable in general to domestic animals, livestock, birds and fish. For example, the invention may be applied in a veterinary or agricultural setting. The sample comprises nucleic acid which may be DNA or RNA. If the nucleic acid is present in the sample in a suitable form allowing for detection according to the invention, the sample may be used directly. However, typically, nucleic acid is derived, obtained or extracted from the sample. Methods for processing samples containing nucleic acids, extracting nucleic acids and/or purifying nucleic acids for use in detection methods are well-known in the art. Total nucleic acid may be isolated or DNA and RNA may be isolated separately.

Typically, a sample is processed in an appropriate manner such that nucleic acid is provided in a convenient form for contacting with the primers and strand invasion oligonucleotide(s) and optional further reagents. Where the nucleic acid is DNA, the DNA is typically provided in double-stranded form. Where the nucleic acid is an RNA, it is typically converted to cDNA using reverse transcriptase or a polymerase with reverse transcriptase activity. RNA may be useful for bacterial detection, owing to the very large number of ribosomes present in bacterial cells which effectively amplify the concentration of target sequences. In addition to ribosomal RNA (rRNA), other forms of RNA, for examples transfer RNAs (tRNA), messenger RNAs (mRNA), small interfering RNAs (siRNA), small nuclear ribonucleic acid (snRNA), microRNAs (miRNA) may also be useful for prokaryote and eukaryote detection.

A method of the invention may be used for diagnosis of an infection by a pathogen in a subject, comprising detection of a target nucleic acid sequence from said pathogen. The determination of whether or not the pathogen is present may be in the context of any disease or illness present or suspected of being present in a patient. Such diseases may include those caused by, linked to, or exacerbated by the presence of the pathogen. Thus, a patient may display symptoms indicating the presence of the pathogen, and a sample may be obtained from the patient in order to determine the presence of pathogen by the method described above.

Any pathogen may be detected. The pathogen may be a virus or bacterium or parasite. The pathogen may be a pathogen such as, but not limited to, fungi, viruses including Human Papilloma Viruses (HPV), HIV, HSV2/HSV1, Influenza virus (types A, B and C), Polio virus, RSV virus, Rhinoviruses, Rotaviruses, Hepatitis A virus, Norwalk Virus Group, Enteroviruses, Astroviruses, Measles virus, Parainfluenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *Mycobacterium tuberculosis, Chlamydia, Neisseria gonorrhoeae, Shigella, Salmonella, Vibrio cholerae, Treponema pallidum, Pseudomonas, Bordetella pertussis, Brucella, Franciscella tularensis, Helicobacter pylori, Leptospira interrogans, Legionella pneumophila, Yersinia pestis, Streptococcus* (types A and B), Pneumococcus, Meningococcus, *Haemophilus influenza* (type b), *Toxoplasma gondii*, Campylobacteriosis, *Moraxella catarrhalis*, Donovanosis, and Actinomycosis; fungal pathogens including Candidiasis and Aspergillosis; parasitic pathogens including *Taenia*, Flukes, Roundworms, Amoebiasis, Giardiasis, *Cryptosporidium, Schistosoma, Pneumocystis carinii*, Trichomoniasis and Trichinosis.

Further applications of the methods of the invention include fragment analysis, cloning, and single-nucleotide polymorphism (SNP) detection.

In another aspect of the invention, a target nucleic acid sequence may be amplified to allow for its sequence to be determined. In such an embodiment a nucleic acid sequence whose sequence is partly or entirely unknown may be amplified by provision of suitable binding regions for one or more strand invasion oligonucleotide(s) flanking the region whose sequence is to be determined. The invention accordingly provides a method of determining the sequence of a target nucleic acid comprising a region of unknown sequence, comprising creating a target nucleic acid sequence comprising strand invasion oligonucleotide binding regions upstream and downstream of said region of unknown sequence, amplifying said target nucleic acid sequence in accordance with an amplification method of the invention described above, and determining the sequence of said region of unknown sequence. The invention further provides a method of amplifying a target nucleic acid sequence comprising a region of unknown sequence comprising creating a target nucleic acid sequence comprising strand invasion oligonucleotide binding regions upstream and downstream of said region of unknown sequence, and amplifying said target nucleic acid sequence in accordance with an amplification method of the invention described above. The target nucleic acid sequence comprising upstream and downstream strand invasion oligonucleotide binding regions may be created by ligation of oligonucleotides comprising strand invasion oligonucleotide binding regions to the 5' and/or 3' ends of a nucleic acid sequence of interest. Alternatively, a nucleic acid sequence of interest may be inserted or ligated into a suitable nucleic acid vector, such as a plasmid, which comprises the strand invasion oligonucleotide binding regions flanking the site at which the nucleic acid sequence is to be introduced, thereby creating the target nucleic acid sequence. In other embodiments, the sequence to be determined may be partially known, such that one species of strand invasion oligonucleotide (and its respective primer) may be designed to bind to the region of known sequence, and the other species of strand invasion oligonucleotide and primer to bind an adaptor sequence introduced flanking the region of unknown sequence. Strand invasion-based amplification upstream of the known sequence and downstream of the unknown sequence may then be used to amplify the region of unknown sequence, such that its sequence can be determined.

The oligonucleotides comprising strand invasion oligonucleotide binding regions are suitably DNA adaptors, typically provided in double-stranded form, with or without overhangs. The adaptor is generally blunt ended when provided as a double-stranded oligonucleotide, to permit its ligation to a DNA fragment of interest. The oligonucleotides comprising strand invasion oligonucleotide binding regions may further comprise primer binding regions. A single species of oligonucleotide comprising a strand invasion oligonucleotide binding region (and optionally also a primer binding region) may be provided where the same species of strand invasion oligonucleotide (and optionally the same species of primer) is used to invade the target nucleic acid sequence at upstream and downstream locations.

The determination of the sequence of the target nucleic acid may be carried out using any suitable sequencing method. Suitable sequencing methods include Sanger sequencing or next generation sequencing methods like Ion Torrent, SOLiD, Illumina and 454 sequencing. Fragments to be sequenced can be preamplified directly from their attached adaptors or can be cloned into sequencing plasmids first. In the latter case the cloned fragment may contain adaptor sequence(s) or these can be provided by the plasmid the fragment is ligated into.

Any suitable adaptor sequence may be used which permits binding of a strand invasion oligonucleotide and/or a primer when incorporated at a position flanking or within a target nucleic acid sequence to permit amplification of the target nucleic acid sequence. The adaptor sequence incorporated at a position flanking or within the upstream region of the target nucleic acid sequence will typically be identical to the adaptor sequence incorporated at a position flanking or within the downstream region of the target nucleic acid sequence. However, different adaptor sequences may be used for the upstream and downstream ends of the target nucleic acid sequence provided that one or more strand invasion oligonucleotides and one or more primers capable of amplifying the target nucleic acid sequence based on the different adaptors are provided. The skilled person is able to select an appropriate adaptor sequence for a particular target sequence. Adaptor sequences can be chosen freely so as to not interfere with any sequences potentially present. Adaptor sequences can also be chosen to cater for recombinase preference to pyrimidine. Adaptor sequences can comprise tags for purification or separation prior to amplification or thereafter. Restriction sites or nicking enzyme recognition sites can be added to aid in further processing of the amplicons.

Kits and Compositions

The invention provides a kit or composition comprising at least one upstream and at least one downstream primer for a target nucleic acid sequence, and first and second strand invasion oligonucleotides which have upstream and downstream binding regions in said target nucleic acid sequence.

The invention further provides a kit or composition comprising a strand invasion oligonucleotide which can bind both to an upstream binding region and a downstream binding region in a target nucleic acid sequence, one or more primers capable of amplifying said target nucleic acid sequence and at least one DNA adaptor. The DNA adaptor is typically in double-stranded form. The kit or composition may further comprise a DNA ligase, which can be used to ligate the DNA adaptor to a nucleic acid of interest. The kit or composition may further comprise one or more restriction enzymes. Typically, the upstream and downstream binding region for the strand invasion oligonucleotide includes the sequence of the DNA adaptor, and thus the strand invasion oligonucleotide is capable of binding to at least a portion of the DNA adaptor. The strand invasion oligonucleotide is capable of rendering upstream and downstream binding regions for the one or more primers single-stranded. The one or more primers thus bind to regions in the target nucleic acid sequence proximal to the strand invasion oligonucleotide binding regions. The one or more primers may also bind to the sequence of the DNA adaptor, such that the DNA adaptor provides the mechanism both for strand invasion and amplification of the unknown sequence. The kit or composition may comprise a single species of primer which can bind both to an upstream and a downstream binding region in the target nucleic acid sequence (typically an adaptor sequence), or upstream and downstream primers for said target nucleic acid sequence.

In a related aspect, the invention provides a kit or composition comprising a strand invasion oligonucleotide which can bind both to an upstream binding region and a downstream binding region in a target nucleic acid sequence, and one or more primers capable of amplifying said target nucleic acid sequence, wherein the strand invasion oligonucleotide is capable of rendering upstream and downstream binding regions for the one or more primers single-stranded, and wherein the strand invasion oligonucleotide and the one or more primers each bind to a DNA adaptor sequence. The strand invasion oligonucleotide and the one or more primers may thus each be capable of binding an identical DNA adaptor sequence present in upstream and downstream locations in a target nucleic acid sequence. The kit or composition may comprise a nucleic acid vector comprising adaptor sequences flanking a cloning site.

The primer(s) and strand invasion oligonucleotide(s) provided in the above kits or compositions may be any of those described above for use in the relevant methods of the invention. The kits and compositions of the invention may further comprise one or more additional strand invasion oligonucleotides.

The composition may be for example a solution, lyophilisate, suspension, or an emulsion in an oily or aqueous vehicle.

In a kit of the invention, the different oligonucleotide species (such as the primer(s) and strand invasion oligonucleotide(s)) may be provided as a mixture, or in separate containers. The kit may optionally further comprise instructions for use in a method of the invention. Thus, a kit comprising first and second strand invasion oligonucleotides may comprise instructions for use in the method of the invention for amplification of a target nucleic acid sequence which comprises use of first and second strand invasion oligonucleotides. The kit may comprise a means for detection of amplified DNA. The kit may comprise reagents for sequencing DNA.

A kit or composition of the invention may optionally comprise one or more probes that detect amplified DNA. A probe provided in the kit or composition may be any of those described above for use in the methods of the invention.

The kit or composition may optionally comprise one or more of a DNA polymerase, a recombinase, and recombinase accessory proteins. Preferably, the DNA polymerase is Bsu polymerase. Preferably, the recombinase is bacteriophage T4 UvsX, optionally in combination with the recombinase accessory proteins UvsY and gp32. The kit or composition may further comprise dNTPs, suitable buffers and other factors which are required for DNA amplification in the method of the invention as described above. The following Examples illustrate the invention.

EXAMPLES

Example 1 Amplification of Target DNA Using Two Invasion Oligonucleotides

Use of two invasion oligonucleotides in the amplification of an artificial target DNA is shown in FIGS. 1 and 2. All oligonucleotides used were either purchased from MWG Eurofins (Germany) or IDT DNA Technologies (Belgium). All reagents and buffers including creatine kinase and sucrose phosphorylase were purchased from Sigma-Aldrich (St. Louis, Mo., USA). T4 single strand binding protein (gp32) and BSU polymerase were purchased from New England Biolabs (Ipswich, Mass., USA). UvsX and UvsY were purified as previously described [1, 2]. *Thermococcus gammatolerans* RNase HII was purchased from GeneSys Ltd (United Kingdom)

Isothermal DNA amplification reactions were performed at 40° C. for at least 90 minutes. Reaction volume was 20 µl, unless otherwise stated. The buffer solution for the reactions was 10 mM Tris-acetate pH 8.0, 10 mM Magnesium acetate, 5% DMSO, 5% PEG 1000, 4 mM DTT, 0.5 mM EDTA, 0.1 mg/ml BSA, 150 mM Sucrose, 2 mM ATP, 200 µM DNTPs, 1:100000 SybrGreen I, 60 mM Tris-Phosphocreatine. Proteins included in the buffer were 250 ng/µl gp32, 5 µM UvsX, 0.0625 U/µl BSU, 0.0125 U/µl sucrose phosphorylase, and 0.025 U/µl creatine kinase. The concentration of each primer and invasion oligonucleotide was 200 nM, unless otherwise stated. The invasion oligonucleotides were designed to bind either in a parallel or an anti-parallel configuration to the target duplex (FIG. 1). The reactions were started by adding magnesium acetate together with or separately from the target DNA, which was present at either 10 fM or 1 pM. Real-time detection of amplification was performed by using an Agilent MX pro-instrument. The instrument was programmed with cycles of 40° C. for 60 seconds with fluorescence of each cycle was detected. The specificity of reaction products was assessed by performing melt analysis immediately after the cycles. This was done by heating the reaction rapidly to 95° C. for 15 seconds, followed by a rapid cooling step to 25° C. for 60 seconds. Then, the reactions were slowly heated from 25° C. to 85° C., with fluorescence measured at 0.5° C. intervals.

Figure 2A:
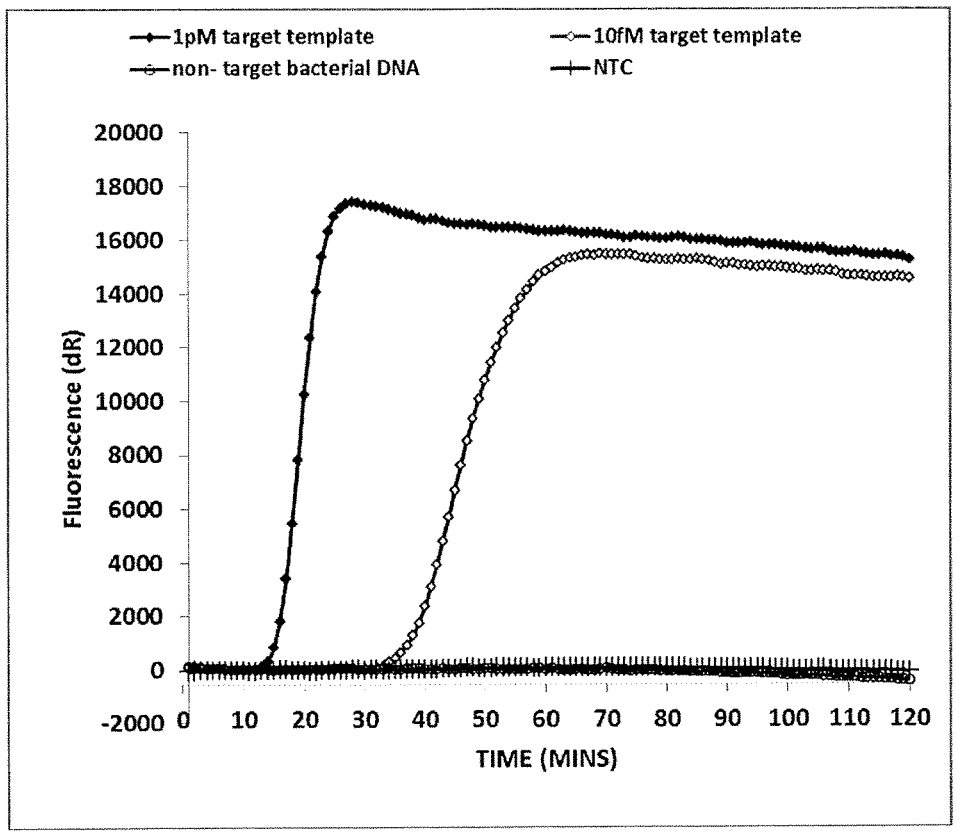
FIG. 2: Amplification of a target DNA using two invasion oligonucleotides. Amplification plots are shown with for (a) parallel invasion oligonucleotide configuration, (c) anti-parallel invasion oligonucleotide configuration and (e) anti-parallel reverse invasion oligonucleotide configuration. Duplicate reactions presented. Amplification was monitored by detecting Sybr Green I. X-axis for amplification plots: time (minutes), Y-axis: SybrGreen I fluorescence (fluorescence intensity, arbitrary units). Specificity of the reactions were further assccessed with melt-curve analyses. Melt curve analyses are shown in (b) for parallel invasion oligonucleotide configuration. (d) for anti-parallel invasion oligonucleotide configuration and (f) for anti-parallel reverse invasion oligonucleotide configuration. X-axis for melt curve analyses: Temperature (degrees Centigrade), Y-axis (−d(fluorescence/d(temperature), (arbitrary units).
Figure 2B:
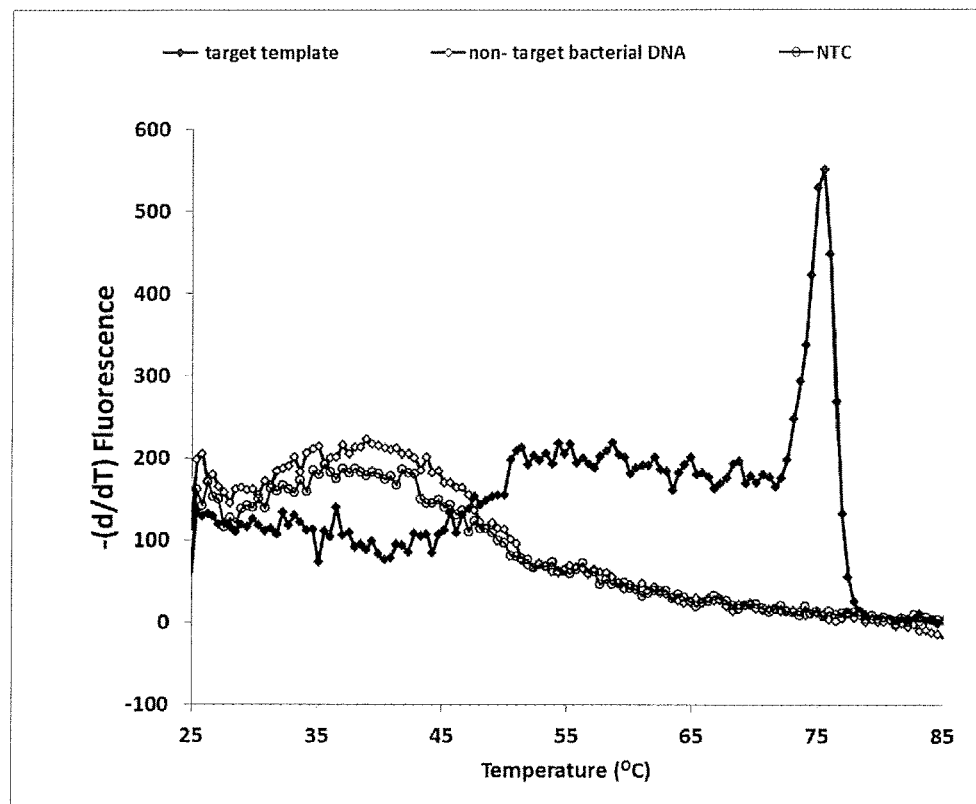

For the parallel configuration, two invasion oligonucleotides (SEQ ID NO: 1 and 2) and forward (SEQ ID NO: 3) and reverse (SEQ ID NO: 4) primers were used. Amplification was only detected in reactions that contained a target DNA comprising the sequence of SEQ ID NO: 11. Reactions without the target DNA (no template control, NTC) did not produce amplification as detected by the absence of Sybr Green I signal (FIG. 2a). Specificity of the parallel configuration was further demonstrated by adding a mixture of genomic DNA from 15 bacteria species which do not contain the target DNA (1000 copies of genomic DNA per reaction was added per species). Amplification was not detected in this mixture, further demonstrating that this configuration detect only the target DNA. Melt analysis with Sybr Green I further confirmed that specific amplification reactions occurred in reaction tubes containing the target DNA (FIG. 2b)

Figure 2C:
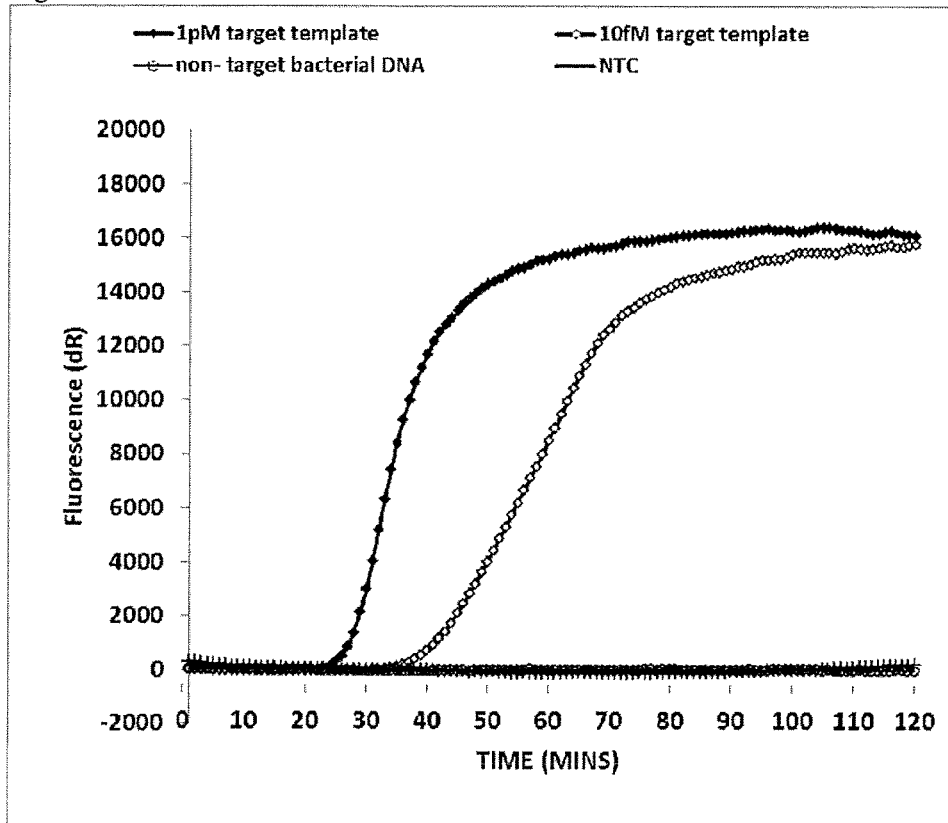
Figure 2D:
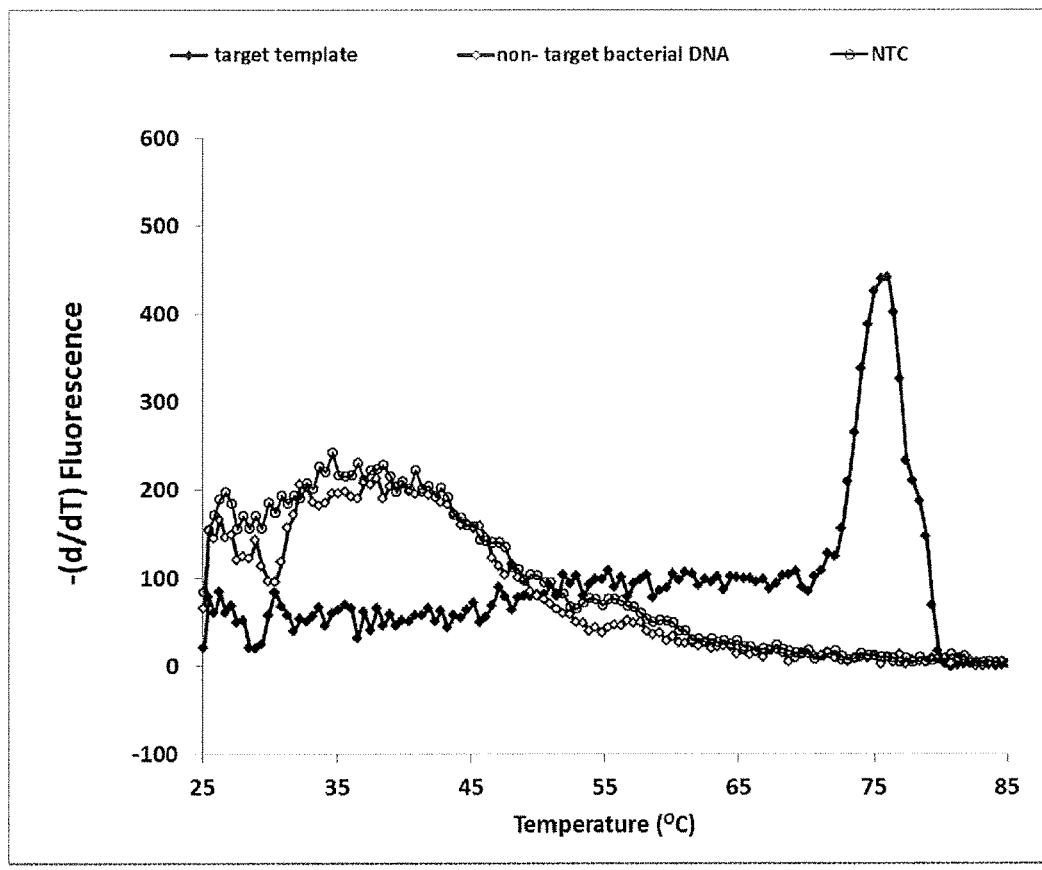

For the anti-parallel configuration, two invasion oligonucleotides (SEQ ID NO: 1 and 2) and forward (SEQ ID NO: 3) and reverse (SEQ ID NO: 5) primers were used. Amplification was only detected when target DNA comprising the target sequence of SEQ ID NO: 12 was added to the reaction (FIG. 2c). In addition, neither the NTC nor the mixture of genomic DNA from bacteria species resulted in amplification with this configuration. Melt analysis with Sybr Green I confirmed that specific reactions occurred in reaction tubes containing the target DNA (FIG. 2d).

Figure 2E:
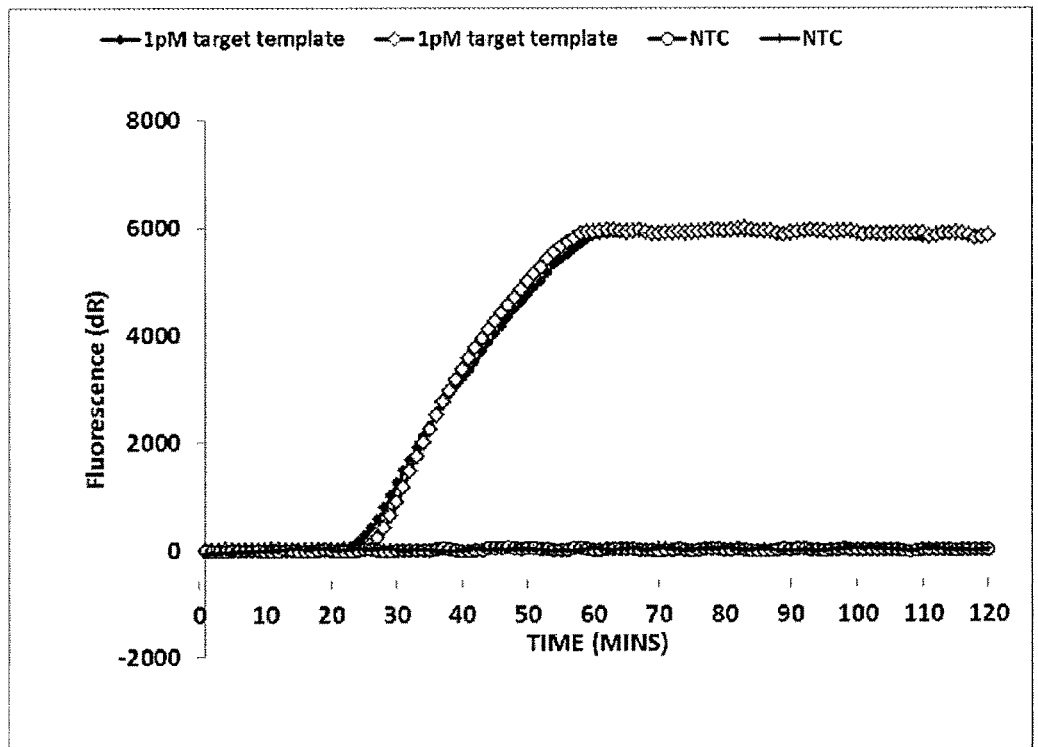
Figure 2F:
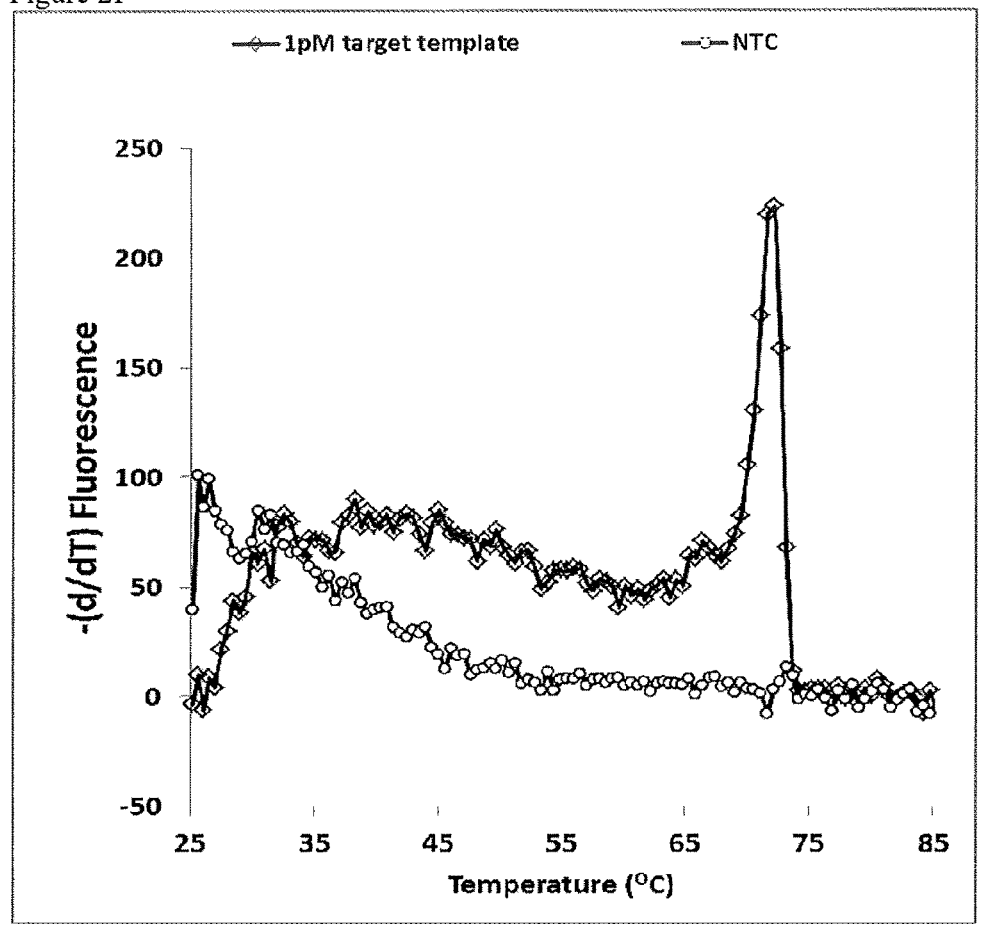

The reverse anti-parallel configuration shown in FIG. 1c was also tested. Two invasion oligonucleotides (SEQ ID NO: 1 and 13) and forward (SEQ ID NO: 14) and reverse (SEQ ID NO: 25) primers were used to amplify a target DNA template comprising the sequence of SEQ ID NO: 26. Amplification was only detected when the target DNA was added to the reaction (FIG. 2e). No detectable signal was observed in the sample in the absence of target DNA. Melt analysis with Sybr Green I further confirmed that specific reactions occurred in reaction tubes containing the target DNA (FIG. 2f)

Example 2 Requirement of Invasion Oligonucleotides for Amplification

Figure 3A:
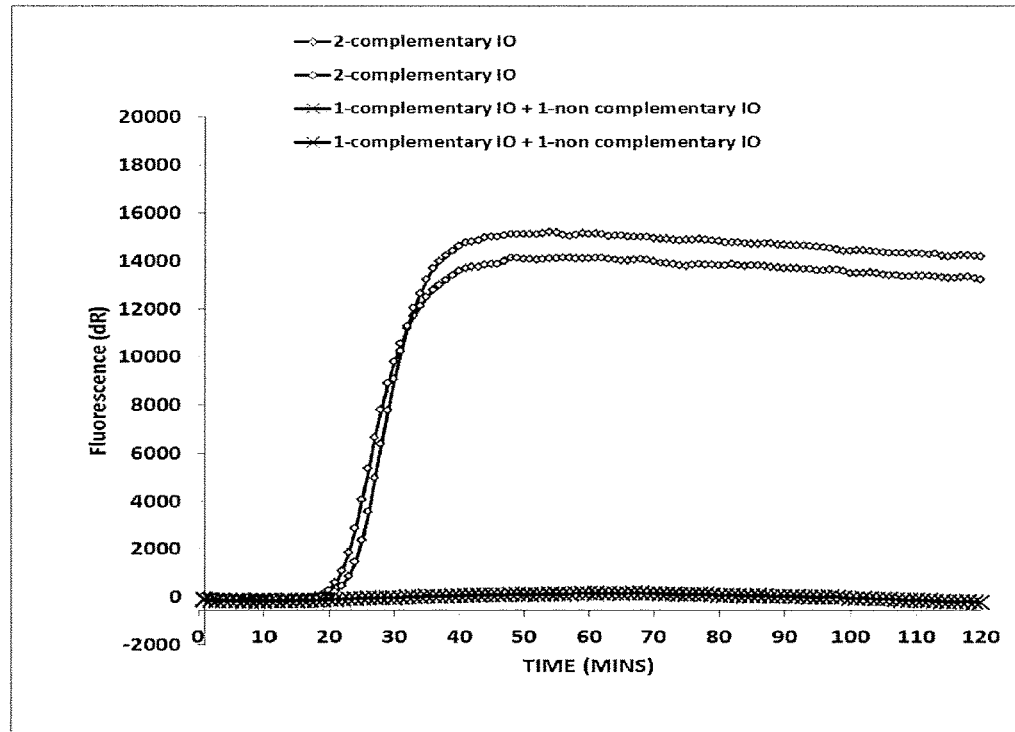
FIG. 3: Amplification of target DNA using two invasion oligonucleotides. Reactions were either performed with two complementary invasion oligonucleotides or with one complementary invasion oligonucleotide and one non-complementary invasion oligonucleotide. X and Y-axis for amplification plots as for FIG. 2. (a) shows results with parallel configuration of oligonucleotides used. (b) shows results with anti-parallel configuration of oligonucleotides. Duplicate reactions presented.
Figure 3B:
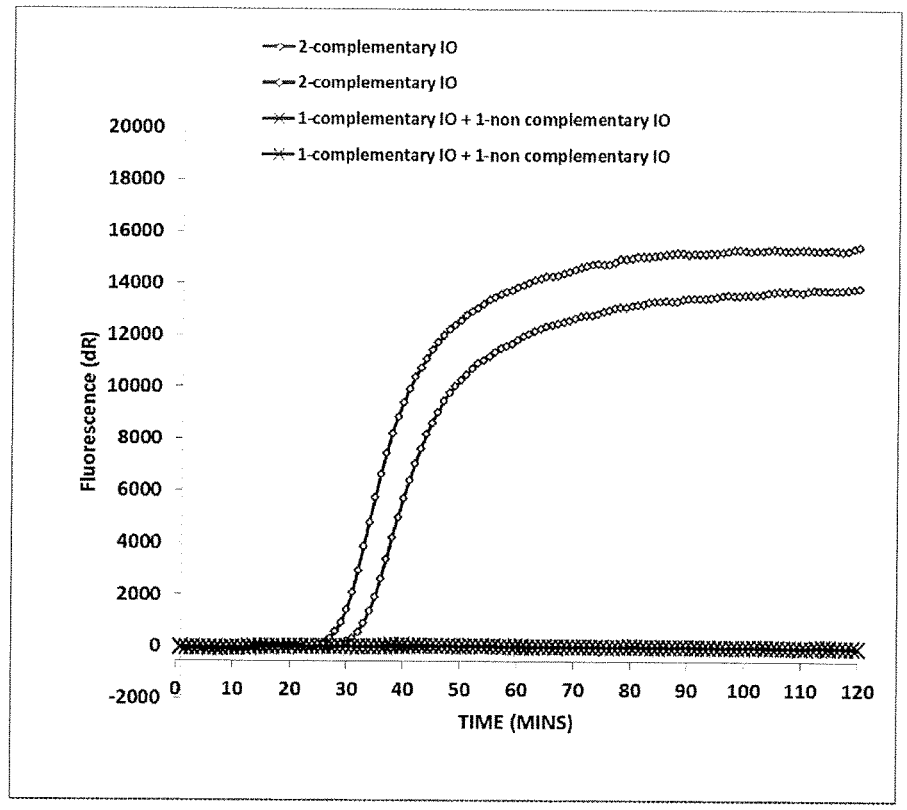

Both invasion oligonucleotides were required for exponential amplification of the target DNA. This was demonstrated by using either two invasion oligonucleotides complementary to the target DNA sequence or with one complementary and one non-complementary invasion oligonucleotide. In the parallel (FIG. 3a) and the anti-parallel (FIG. 3b) configurations, the other invasion oligonucleotide (SEQ ID NO: 1) complementary to the target DNA sequence was replaced with a non-complementary invasion oligonucleotide (SEQ ID NO: 6). Primers and reagents used for both configurations were as described in Example 1. Amplification reactions were performed in the presence of 1 pM target DNA. The target DNA only amplified when both invasion oligonucleotides were complementary to the target DNA sequence (FIG. 3). This also suggests that the amplified product contains the full length of the target template. Furthermore, the NTC or the replacement of complementary invasion oligonucleotide with a non-complementary one, did not result in amplification. This demonstrates that primers do not amplify the target DNA in the absence of the invasion oligonucleotide.

Example 3 Requirement of Primers for Amplification

Figure 4:
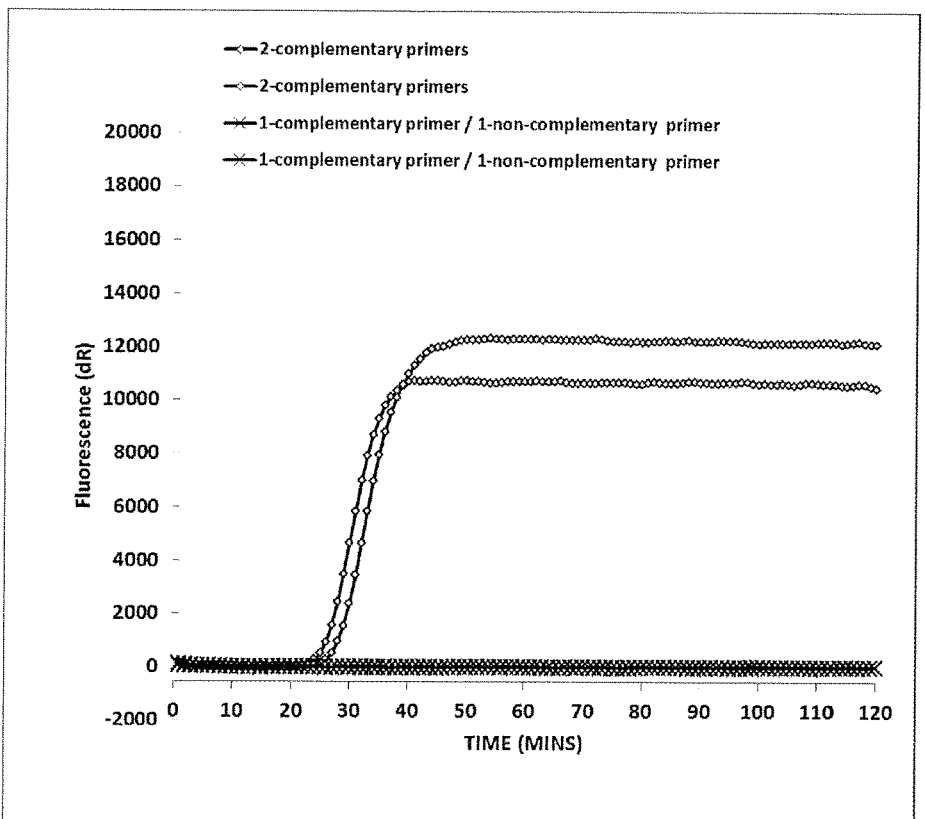
FIG. 4: Specificity of primers in the amplification reaction using two invasion oligonucleotides. Reactions were performed either with complementary forward and reverse primers or with complementary forward and non-complementary primer. Concentration of target DNA was 1 pM. X and Y-axis for amplification plot as for FIG. 2.

Forward and reverse primers are required for amplification of the target DNA. This was demonstrated by substituting one of the primers complementary to the target DNA with a non-complementary primer. Amplification reactions were performed either in the presence of the reverse primer (SEQ ID NO: 4) or in the presence of a reverse primer non-complementary to the target DNA (SEQ ID NO: 7). Concentration of the target DNA was 1 pM. Amplification was only detected in reactions containing the reverse primer (SEQ ID NO: 4) complementary to the target DNA (FIG. 4). In reactions where the complementary reverse primer (SEQ ID NO: 4) was substituted with the non-complementary reverse primer (SEQ ID NO: 7) no amplification was detected. This indicates that invasion oligonucleotides do not amplify the target DNA sequence independently due to their inability to act as polymerase substrates. Furthermore, this demonstrates that all oligonucleotides are required for amplification to occur.

Figure 5A:
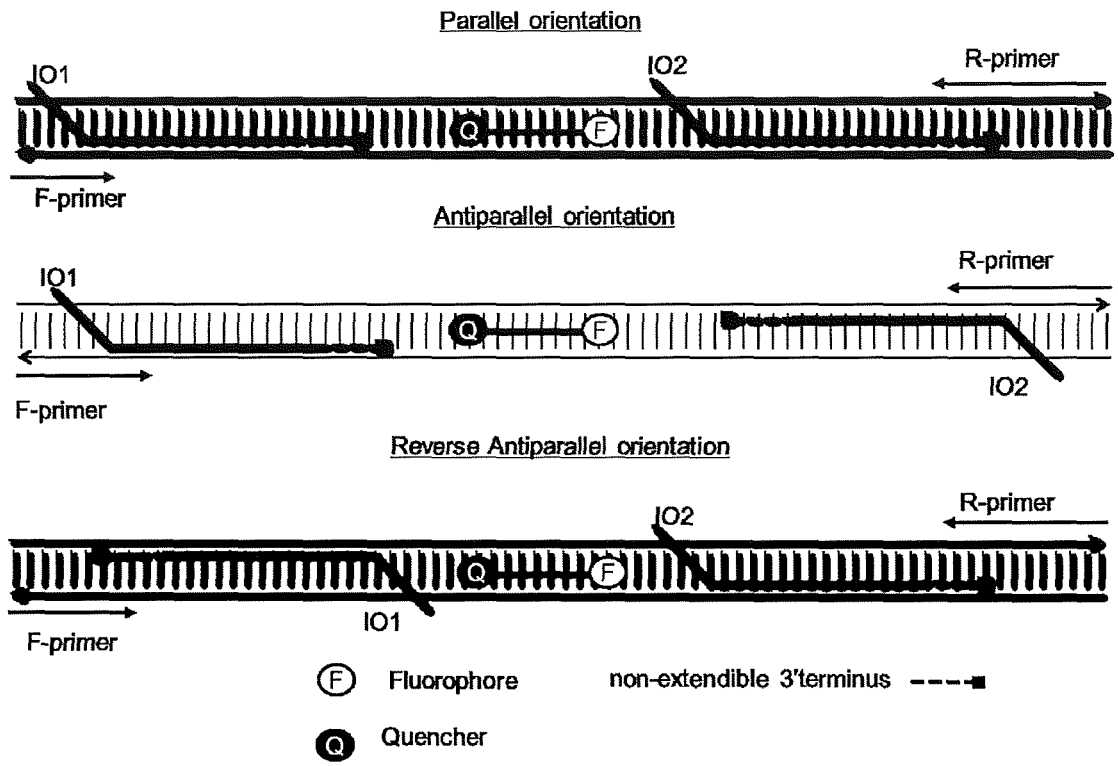
FIG. 5: Compatibility of reaction using two invasion oligonucleotides with target specific probes. (a) shows schematic representation of configurations supporting the use of target specific probes. (b) and c) show amplification and real-time detection of target DNA with either (b) two invasion oligonucleotides or (c) a single strand invasion oligonucleotide (SIBA). Real-time monitoring of amplification was achieved either with Sybr green I or a target specific probe, as shown in the labels for the traces. X-axis for each chart: Time (minutes). Y-axis: fluorescence of Sybr green I or probe (arbitrary units).
Figure 5B:
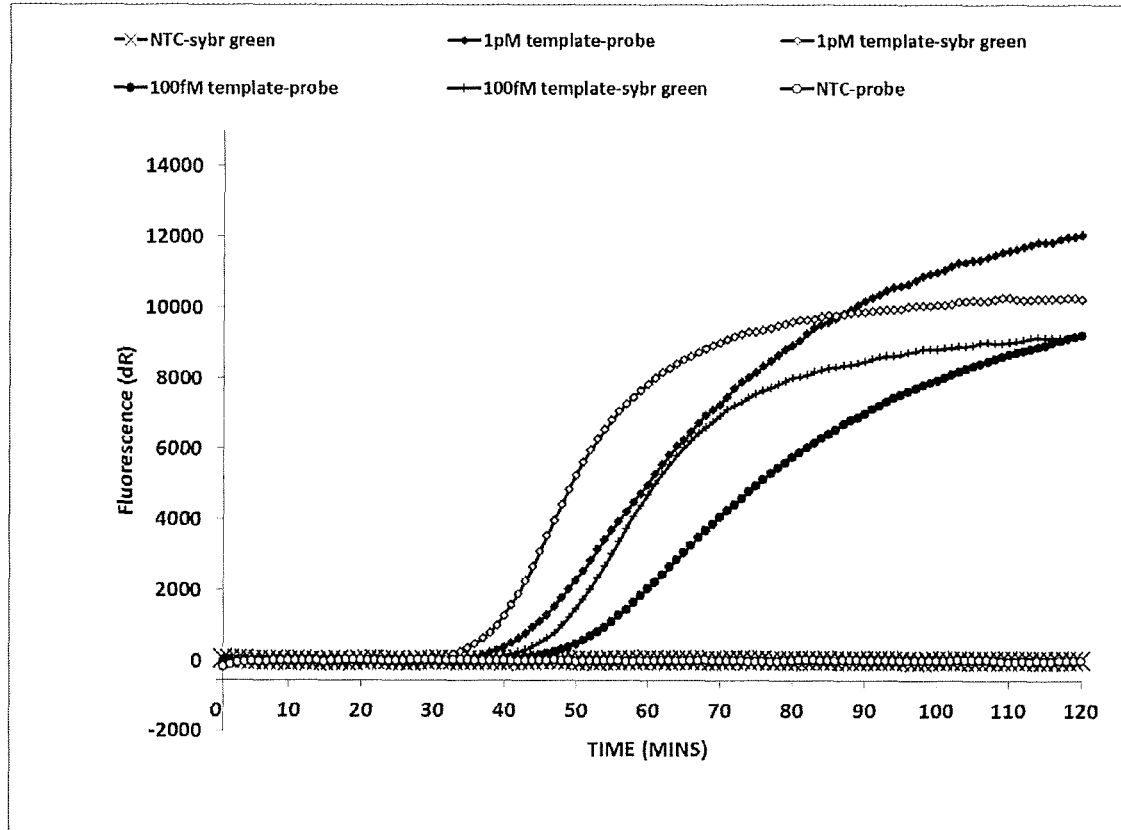

Example 4 Target Specific Probe Compatibility with Two Invasion Oligonucleotides Strand invasion based amplification with two invasion oligonucleotides allows improved possibilities to design target DNA specific probes. In both parallel and anti-parallel configurations there are regions on the target DNA that are neither complementary to the invasion oligonucleotides nor to the primers. This implies that additional probes can be designed to bind these regions without competing with the invasion oligonucleotides or the primers (FIG. 5a). Amplification in the anti-parallel configuration was tested in the presence of the target specific probe. The probe comprises a fluorophore and a quencher separated by an RNA base. The probe is also blocked at the 3'-end to further ensure that non-specific extension does not occur. Concentration of the invasion oligonucleotides (SEQ ID NO: 1 and 2) was 200 nM, while concentration of the primers (SEQ ID NO: 3 and 4) and the probe (SEQ ID NO: 8) was 400 nM. Standard amplification reaction was conducted as described in Example 1 in the presence of 10 µg/ml of *Thermococcus gammatolerans* RNase H2. Real-time amplification was detected with either Sybr Green I or with the probe labelled with a fluorophore and a quencher (FIG. 5b). This shows that the probe binds efficiently to the target DNA during the reaction and produces a detectable signal.

Figure 5C:
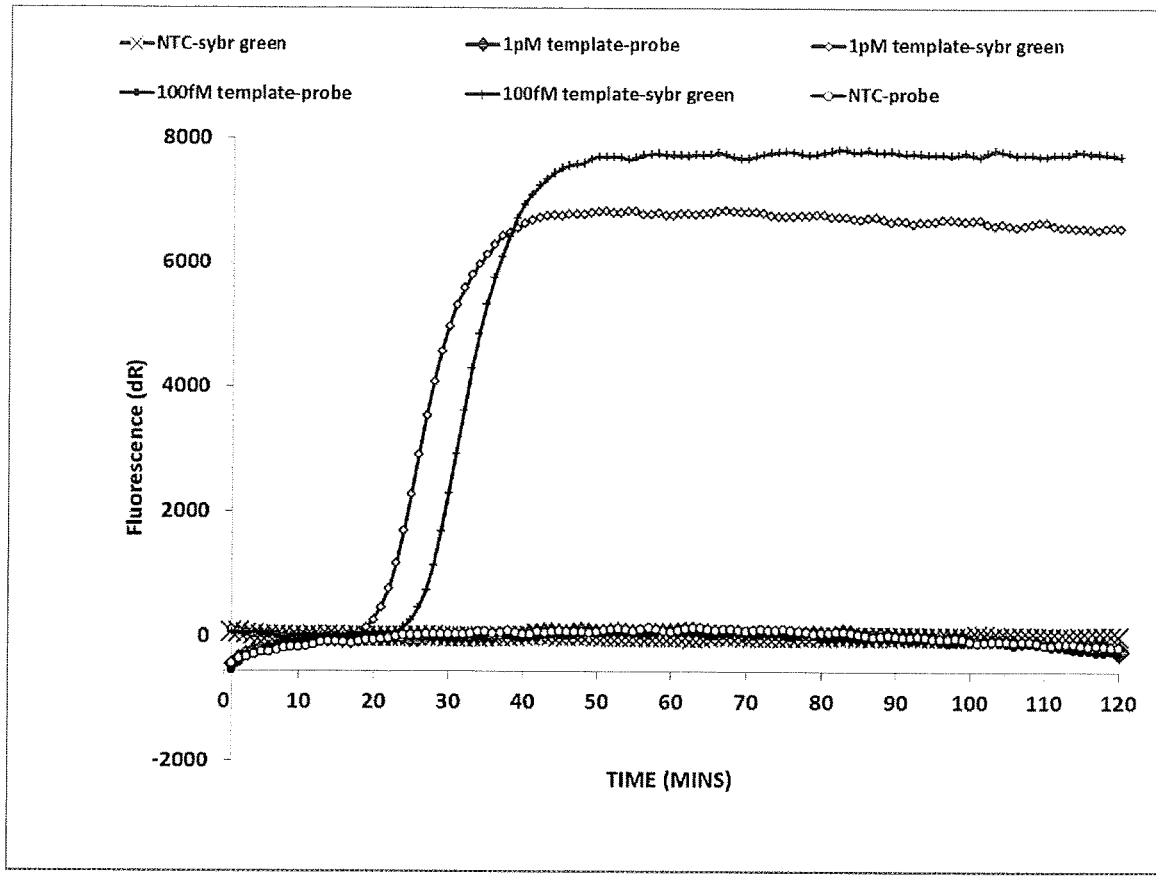

In previously described strand invasion based amplification using only one invasion oligonucleotide, (SIBA) designing of probe chemistry is complex, because the configuration does not readily support a free binding of probe on the target DNA region. This is because all regions of the target DNA typically either serve as a binding site for the invasion oligonucleotide or the primers. Thus the target specific probe will have to compete with the invasion oligonucleotide and the primers for binding, unless specially designed. The results shown in FIG. 5c illustrated the problem associated with using a target specific probe specific for the same target region as the invasion oligonucleotide in SIBA. In the SIBA assay, invasion oligonucleotide (SEQ ID NO: 1), forward primer (SEQ ID NO: 3), and reverse primer (SEQ ID NO: 5) concentrations were 200 nM, while probe (SEQ ID NO: 9) concentration was 400 nM. Real-time amplification was monitored with either Sybr Green I or the probe (FIG. 5c). The increase in Sybr Green I signal in reaction containing the target DNA showed that amplification occurred. However, with the probe overlapping the invasion oligonucleotide binding site no signal was detected, suggesting that the probe was unable to bind the target DNA. That is likely to be due to competition between the invasion oligonucleotide and the probe.

Example 5 Use of Target Specific Probe in Configuration with Two Invasion Oligonucleotides Reduces Signal of Non-Specific Amplification Created by Short Primers The use of very short primers may lead to non-specific amplification in SIBA due to potential extension of the invasion oligonucleotide. Such a non-specific amplification was detected with certain short primers (14 bases) that can potentially extend the DNA region of the invasion oligonucleotide (FIG. 6b). Thus, in standard SIBA primers are designed to be around 16-23 bases in length and their 3'-ends are partly homologous to the invasion oligonucleotide. In the configuration with two invasion oligonucleotides the amplification method is less prone to detection of non-specific amplification products from short primers. This is due to the fact that a probe binding site can be used which is not overlapping with the binding sites of either of the invasion oligonucleotides or the primers.

Figure 6A:
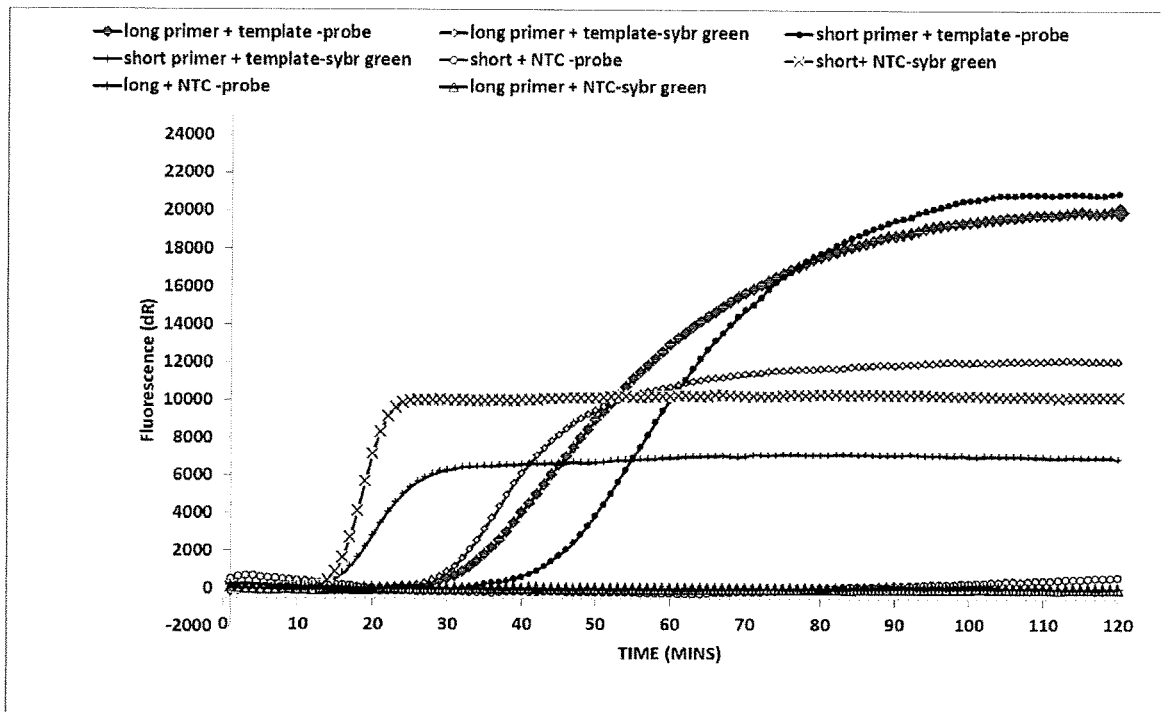
FIG. 6: Resistance of (a) reaction using two invasion oligonucleotides and (b) standard reaction using a single strand invasion oligonucleotide (SIBA) to detection of non-specific amplification. Standard SIBA is was less resistant to detection of non-specific amplification with short primers than amplification carried out with two invasion oligonucleotides. Concentration of target DNA was 1 pM for long primers and 1 fM for short primers. Amplification was monitored using Sybr green I or a probe having a binding site which is non-overlapping with the binding site of the strand invasion oligonucleotides or primers. X-axis for each chart: Time (minutes). Y-axis: fluorescence of Sybr green I or probe (arbitrary units). (a) shows monitoring of amplification with Sybr green I or probe during amplification with two invasion oligonucleotides. (b) shows monitoring of amplification with Sybr green I in SIBA.
Figure 6B:
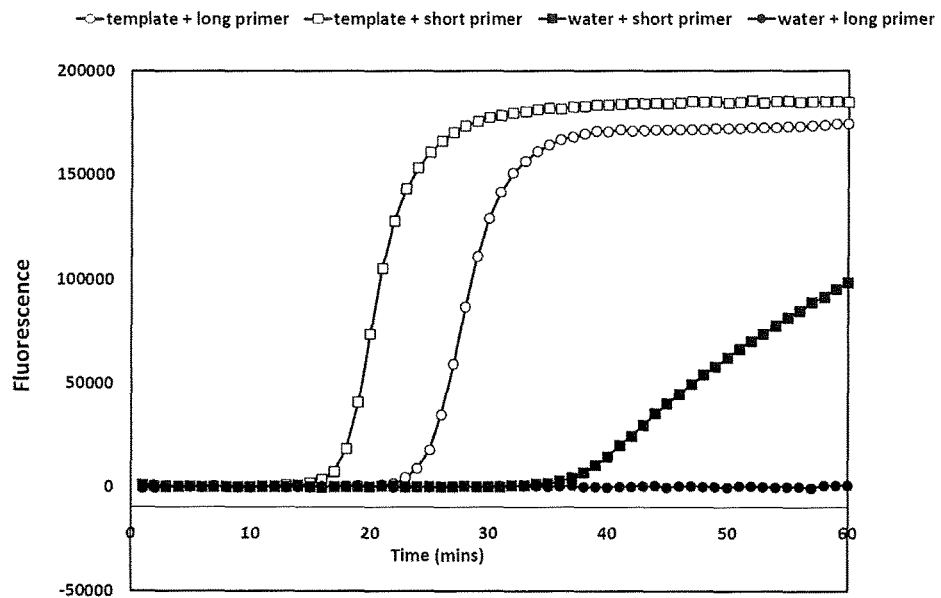

FIG. 6 demonstrates amplification reaction performed with either two invasion oligonucleotides in the anti-parallel configuration or with the conventional SIBA. In both strand invasion based amplification methods, the use of short primers (14 bases in this example) and long primers (in this example 21 bases) led to an increase in Sybr Green I signal with the target template. However, with short primers a small signal was also detected from NTC, while long primers did not produce signal in NTC. The configuration with two invasion oligonucleotides however allowed probe binding to the target sequence without competition with the invasion oligonucleotide and the primers. Such a configuration eliminated detection of the signal created with short primers in NTC (FIG. 6a).

Example 6 Amplification of Plasmid DNA Using Two Invasion Oligonucleotides

Figure 7:
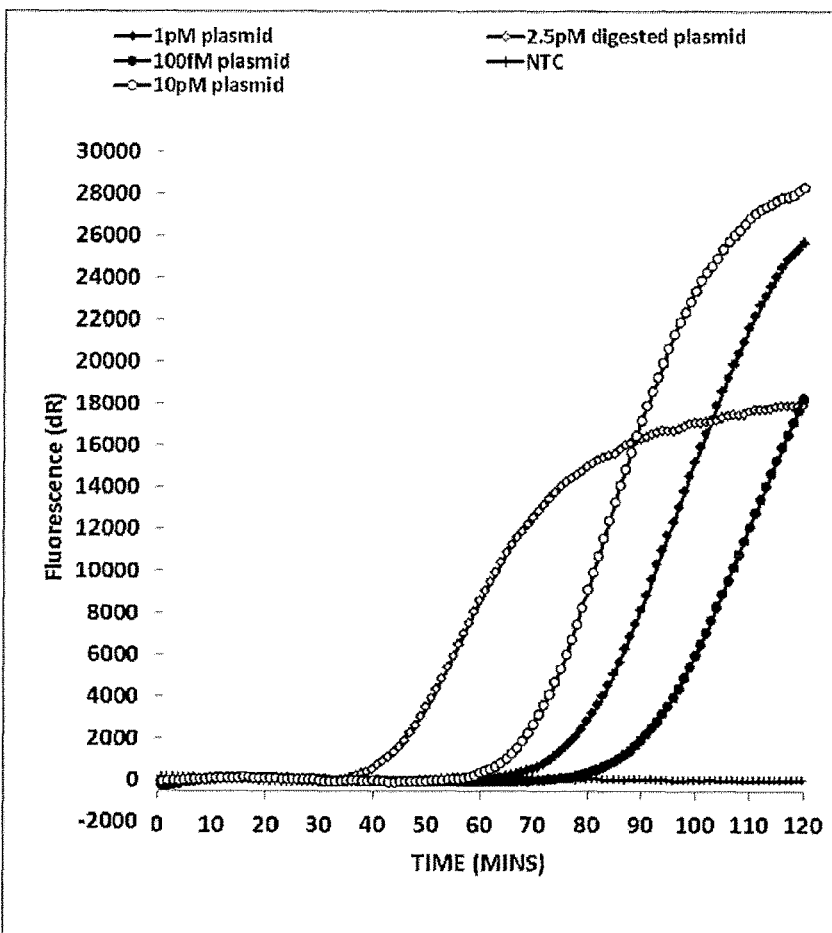
FIG. 7: Amplification of a target DNA from a plasmid DNA using two strand invasion oligonucleotides. Plasmid DNA was either used directly or treated with EcoRV-HF restriction enzyme. Amplification was monitored using Sybr green I. X-axis: Time (minutes). Y-axis: fluorescence of Sybr green I (arbitrary units).

The two invasion oligonucleotide amplification method can be used to amplify different types of DNA templates. The target DNA duplex (target for anti/parallel configuration, SEQ ID NO: 20) was cloned into commercially available pCR2.1 vector MWG Eurofins (Germany). The insert was flanked by EcoRI restriction sites. The plasmid was then used as a template for anti-parallel configuration of two invasion oligonucleotides method as described in Example 1. The concentration of each invasion oligonucleotide, primer and probe was 200, 400 and 600 nM, respectively. Appropriate amounts (100 fM-10 pM) of digested or non-digested plasmid were added to the reaction, as shown in FIG. 7. Digested plasmid was prepared by incubating the target plasmid with EcoRV-HF restriction enzyme (New England Biolabs, Ipswich, Mass., USA) for 3 hours at 37° C. As shown in FIG. 7, the method was able to amplify the target DNA from both digested and undigested plasmid. Plasmid DNA digested with restriction enzyme was however detected earlier than the non-digested plasmid. This may be due to a delay associated with the first round of amplification when circularized plasmids are used as a target template. This also suggests that restriction enzymes could be used for minimizing the lag time during the first round of amplification, when complex DNA are used as the template. This could either be done by first incubating the complex DNA with the appropriate restriction enzymes or by including the restriction enzyme to amplification reagents.

Example 7 Amplification of a Target DNA with Multiple Invasion Site

The target duplex can be designed to have terminal regions containing identical binding sites for invasion oligonucleotides. This implies that only one invasion oligonucleotide is required to dissociate both ends of the target duplex. Such a target duplex mimics a library of unknown DNA fragments that has been ligated with adaptors (known sequence) or where only part of the DNA fragment sequence is known. These unknown DNA fragments can then be amplified by using adaptor specific primers. The amplified products then serve as a template for downstream applications such as DNA sequencing. Such a system can also be used for other downstream applications such as fragment analysis, cloning, single-nucleotide polymorphism (SNP) detection. DNA fragments can be efficiently amplified using two identical target sequences for a single invasion oligonucleotide in parallel, anti-parallel or reverse anti-parallel configurations (FIG. 8). In this example, standard amplification reaction was conducted as described in Example 1 except that 5% PEG 1000 was replaced with 7.5% PEG 400.

Figure 8A:
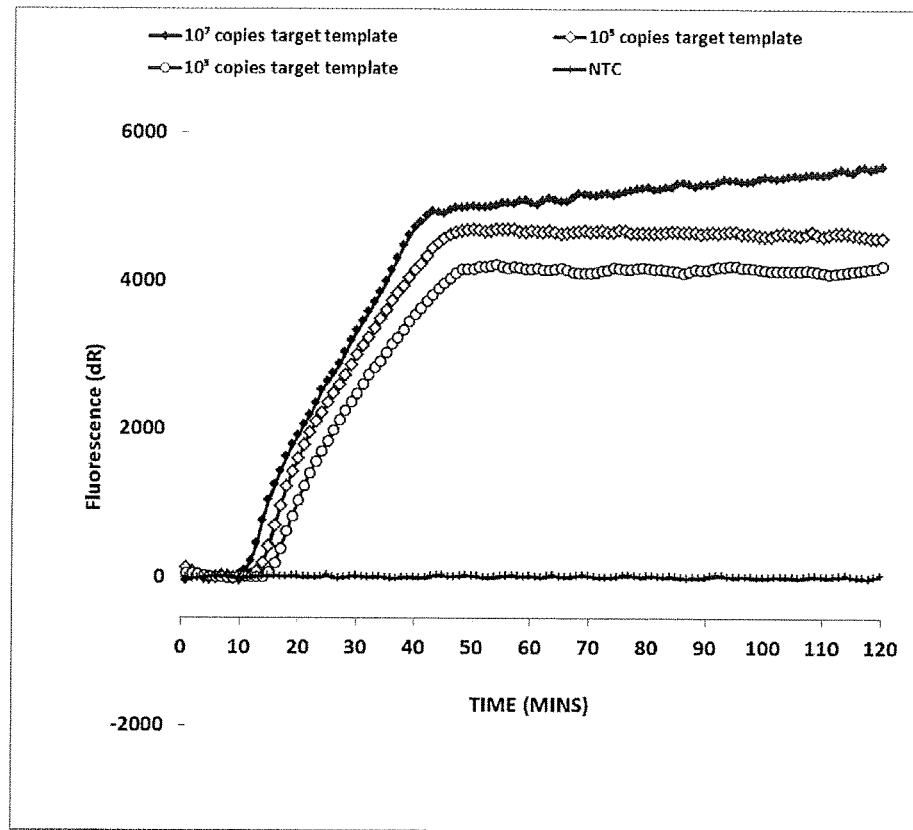
FIG. 8: Amplification of a target DNA having two identical invasion sites. Reactions were performed with a single invasion oligonucleotide that binds to both invasion sites of the target DNA. (a), (c), (e) and (g) show amplification plots for real-time monitoring of target DNA amplification using Sybr green I. (b), (d), (f) and (h) show corresponding melt curve analyses. (i) shows non-denaturing electrophoresis of reaction products. a) and b): parallel configuration of invasion oligonucleotides used to amplify a 324 base pair a duplex target DNA. (c) and (d): parallel configuration of invasion oligonucleotides used to amplify a target DNA. (e) and (f): anti-parallel configuration of invasion oligonucleotides used to amplify a target DNA. (g) and (h): reverse anti-parallel configuration of invasion oligonucleotides used to amplify a target DNA. (i) anti-parallel configuration of invasion oligonucleotides used to amplify a target DNA. X and Y-axes for amplification plots and melt curve analyses as for FIG. 2. Real-time monitoring of target DNA amplification was achieved using Sybr green I. (i) Lanes for electrophoretogram as follows: Lane 1, BioRad EZ Load 20 bp Molecular Ruler; lanes 2-6 copied $10^7$, $10^6$, $10^5$, $10^4$ and $10^3$ respectively; lane 7, water control.
Figure 8B:
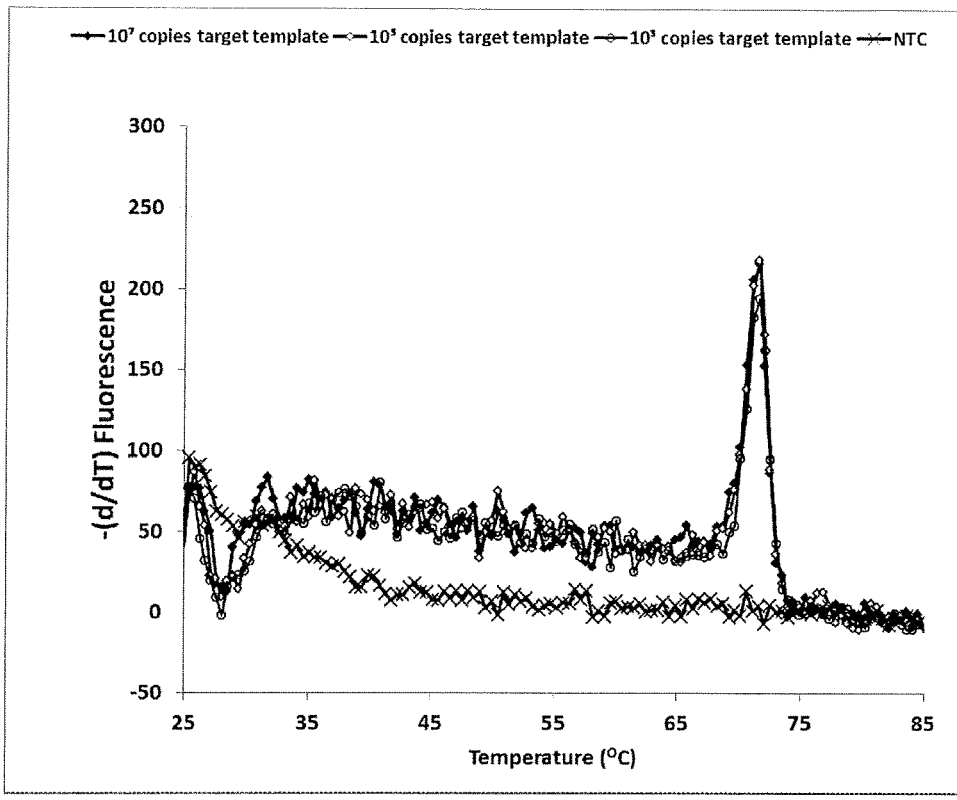

For the parallel configuration, 400 nM of an invasion oligonucleotide (SEQ ID NO: 13), 200 nM forward (SEQ ID NO: 14), and 200 nM reverse primer (SEQ ID NO: 15) were used to amplify an appropriate amount of a 324 bp target duplex DNA (SEQ ID NO: 16). The target duplex (SEQ ID NO: 16) contained a 200 bp human lactase (LCT) gene fragment flanked by sequences that served as binding sites for the invasion oligonucleotide (SEQ ID NOs 28 and 29). Amplification was only detected in reactions that contained the target duplex DNA (SEQ ID NO: 16) and reactions without the target duplex DNA (no template control, NTC) did not produce any detectable Sybr Green I signal (FIG. 8A). The rate of amplification was very fast and efficient with 1000 copies of target DNA being detected within 20 minutes of starting the reaction. Melt analysis with Sybr Green I further confirmed that the reactions were specific (FIG. 8B).

Figure 8C:
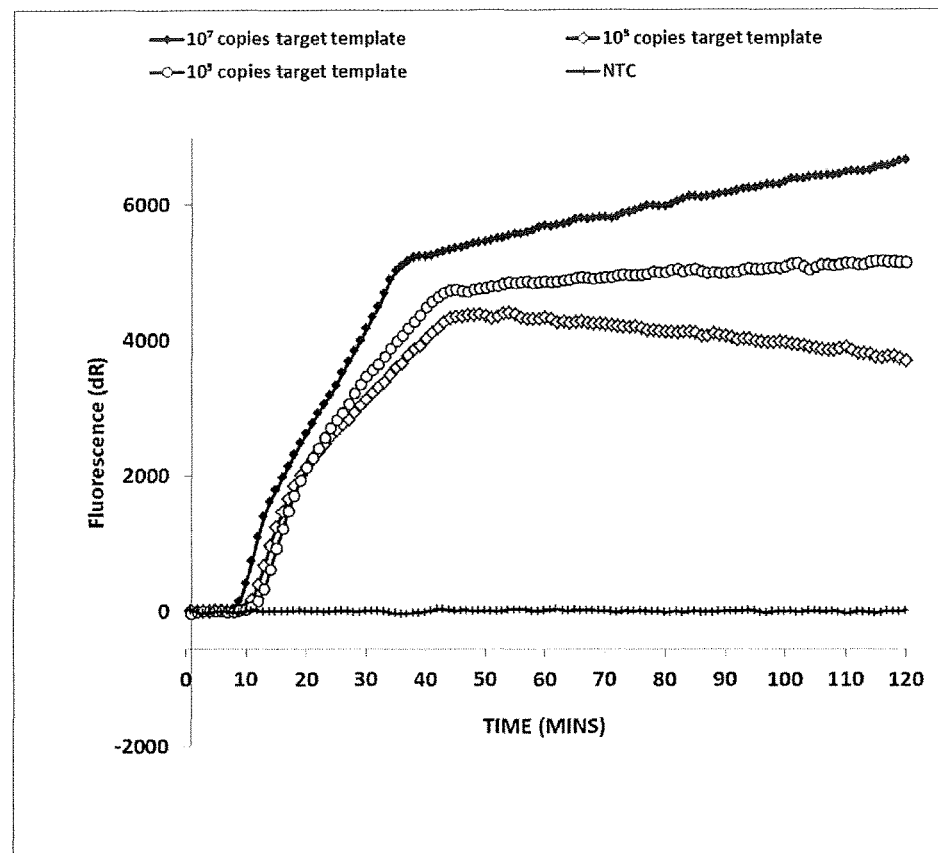
Figure 8D:
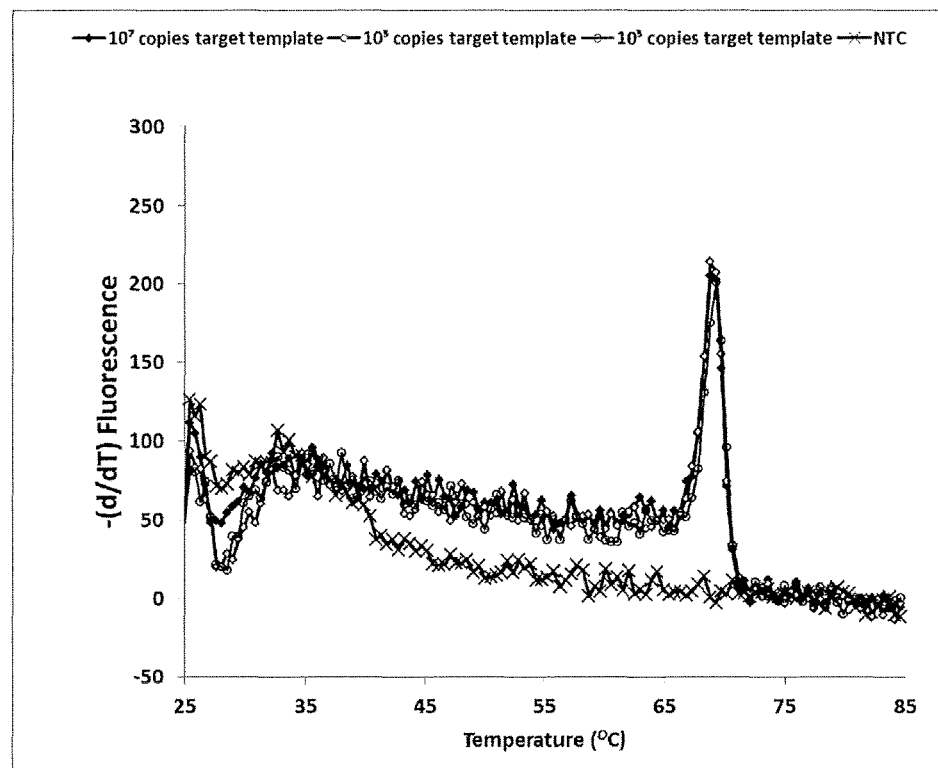

The parallel configuration was further demonstrated by using 400 nM of an invasion oligonucleotide (SEQ ID NO: 2), 200 nM forward (SEQ ID NO: 5), and 200 nM reverse primer (SEQ ID NO: 4) to amplify another target DNA (SEQ ID NO: 17) comprising flanking sequences that served as binding sites for the invasion oligonucleotide (SEQ ID NOs 30 and 31). The reaction displayed similar performance as previously seen in FIG. 8A. Amplification of the target DNA (SEQ ID NO: 17) was also found to be very efficient with a 1000 copies being detected within 20 minutes of starting the reaction (FIG. 8C). Melt analysis with Sybr Green I further confirmed that specific amplification reactions occurred in reaction tubes containing the target DNA (FIG. 8D)

Figure 8E:
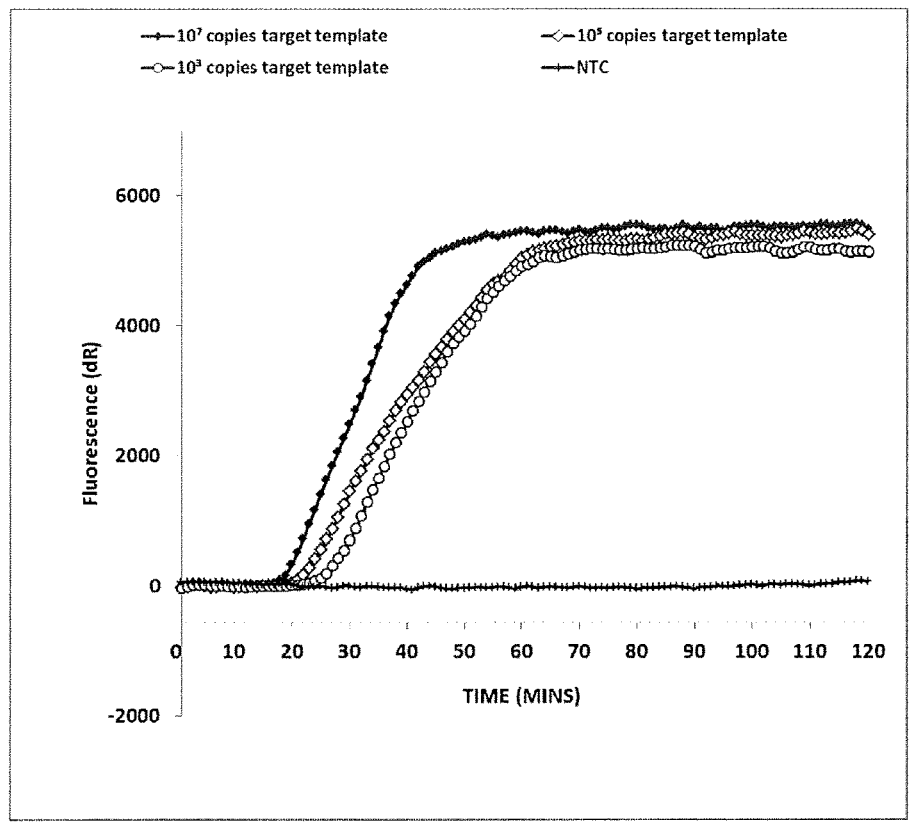
Figure 8F:
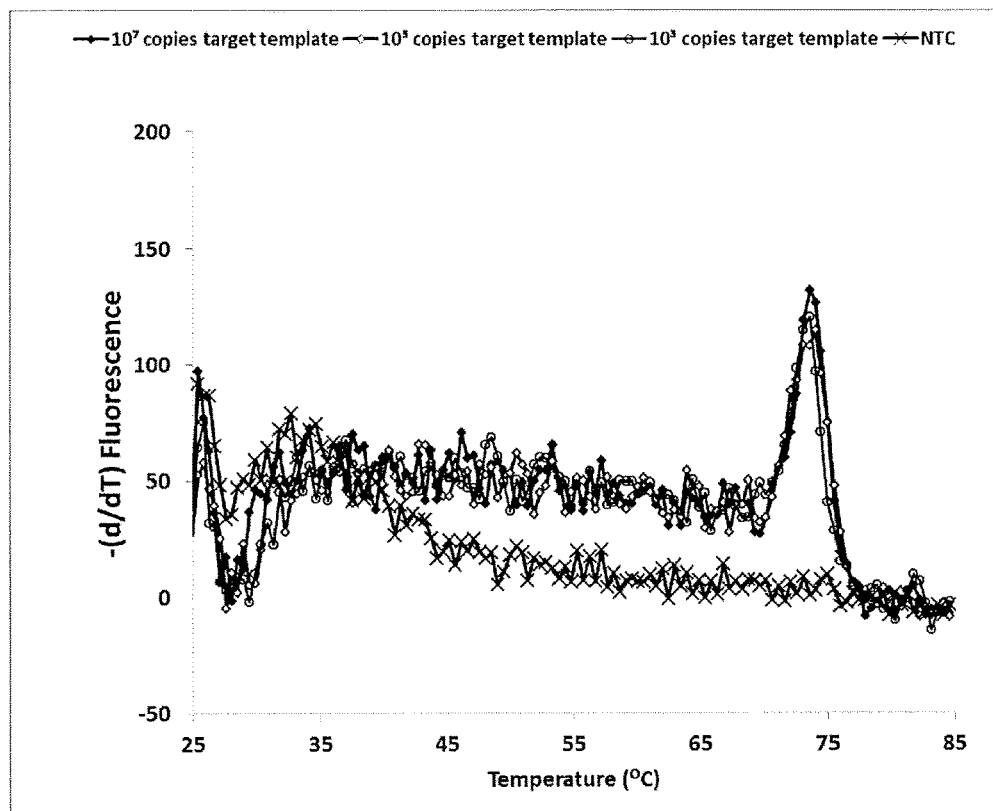

For the anti-parallel configuration, 400 nM of invasion oligonucleotide (SEQ ID NO: 2) and 400 nM primer (SEQ ID NO: 5) was used to amplify a target DNA (SEQ ID NO: 18) comprising an adaptor sequence (SEQ ID NO:27). The primer (SEQ ID NO: 5) served as both the forward and reverse primer. Accordingly, only one IO and one species of primer may be used to amplify a target DNA where appropriate binding sequences are provided. Amplification was only detected in reactions that contained the target DNA (SEQ ID NO: 18). Reactions without the target DNA (no template control, NTC) did not produce any detectable signal with Sybr Green I signal (FIG. 8E). Melt analysis with Sybr Green I further demonstrated that the reaction was target specific. (FIG. 8F).

Figure 8G:
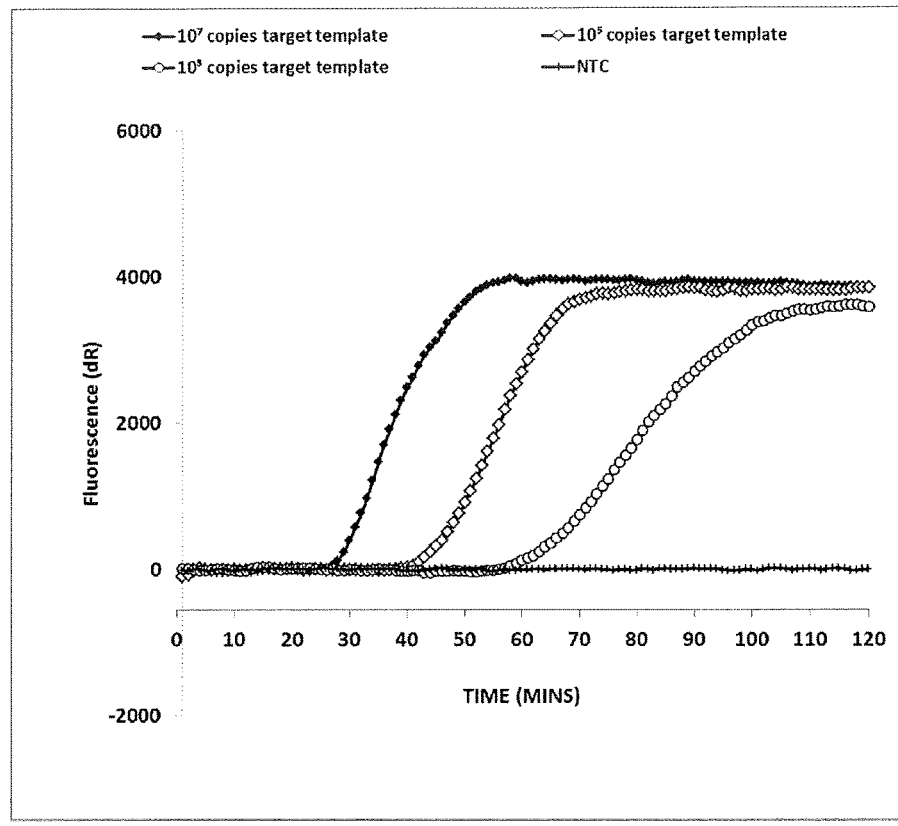
Figure 8H:
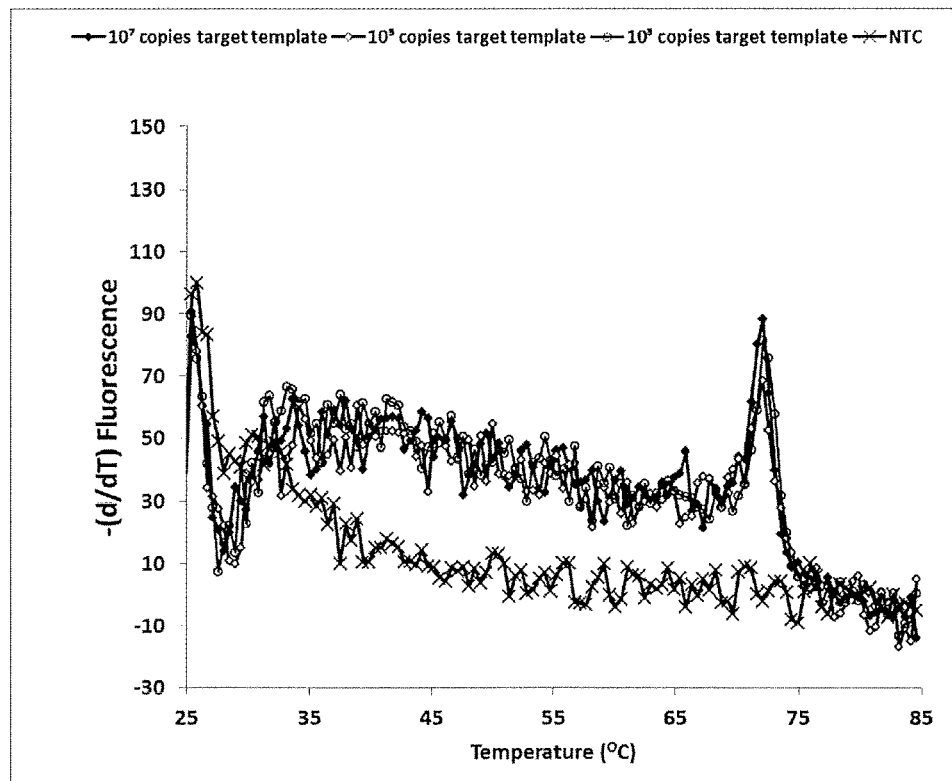

Similar studies were conducted using the reverse anti-parallel configuration. 400 nM of invasion oligonucleotide (SEQ ID NO: 13) and 400 nM primer (SEQ ID NO: 15) was used to amplify the target DNA (SEQ ID NO: 19). The primer (SEQ ID NO: 15) served as both the forward and reverse primer. This configuration was also able to specifically amplify the target DNA and non-specific reactions were not seen in the NTC (FIG. 8G). Melt analysis with Sybr Green I further demonstrated the reaction was target specific (FIG. 8H).

The rate of amplification using the reverse anti-parallel configuration appeared to be slower than the parallel and anti-parallel configurations. The parallel configuration seemed to display the fastest amplification rate. Differences in amplification rate may be mediated by various factors. For example, although all three systems use a similar invasion oligonucleotide, their primers are different. This could account for some differences in amplification rate since the melt temperature and length of primers can impact on amplification rate.

Figure 8I:
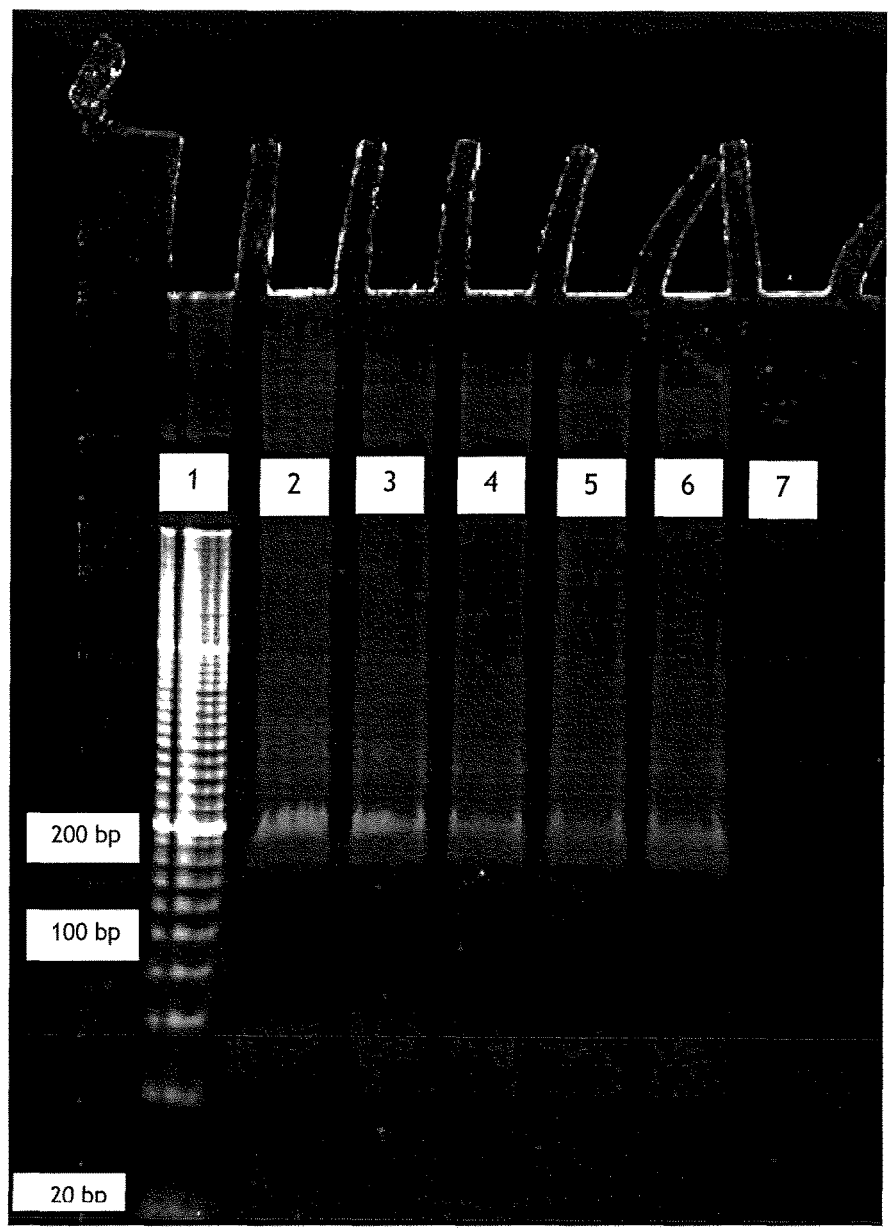

Reactions using the anti-parallel configuration were further subjected to non-denaturing polyacrylamide gel electrophoresis (PAGE) (FIG. 8i). A standard amplification reaction was conducted as described in example 1 except that magnesium acetate was used at 20 mM, 5% PEG 1000 was replaced with 7.5% PEG 400 and the reactions were performed at 44° C. by using a Bio Rad CFX 96 PCR device for 120 minutes. 200 nM of invasion oligonucleotide (SEQ ID NO: 2) and 400 nM primer (SEQ ID NO: 5) was used to amplify appropriate amount of target DNA (SEQ ID NO: 18). The primer (SEQ ID NO: 5) served as both the forward and reverse primer. Accordingly, only one IO and one species of primer were used to amplify the target DNA since appropriate binding sequences are provided. For PAGE, a 5 µl aliquot of the reaction mixture was loaded into a 8% TBE gel (Invitrogen, United Kingdom) and electrophoresed at 150 V (constant) for 60 min. Gels were stained with a fluorescent nucleic acid gel stain (GelRed; Biotium, United States) and visualized using a Gel Doc™ EZ System (Bio-Rad, United Kingdom). A distinct band corresponding to the expected length of amplification product appeared only in reactions that contained the target template. No band was detected in samples without the target template, demonstrating that non-specific amplification products were absent.

Figure 9A:
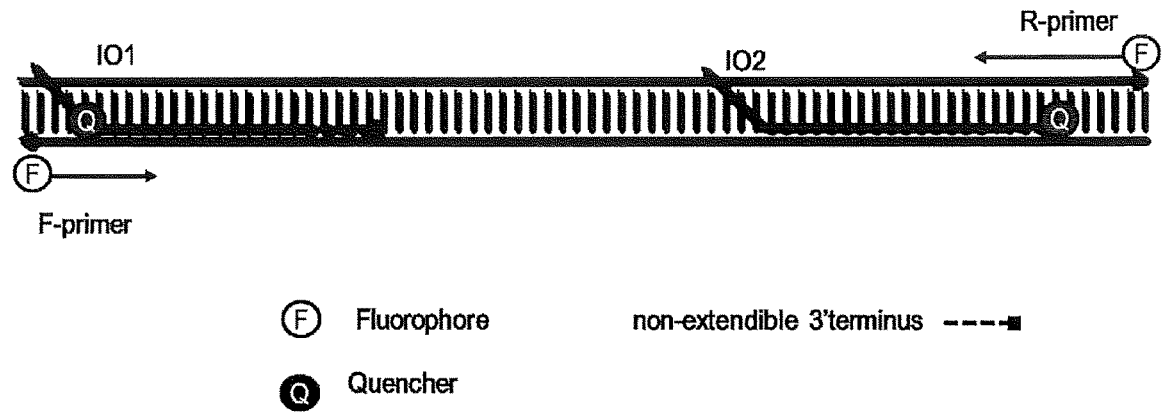
FIG. 9: FRET based system for real-time monitoring invasion and amplification: (a) schematic representation of labelled primers and invasion oligonucleotides. (b) Real time monitoring of invasion and amplification and detection of target DNA using FRET labelled oligonucleotides in parallel configuration. X-axis for (b): Time (minutes). Y-axis: fluorescence of probe (arbitrary units).

Example 8 FRET Based Probes for Monitoring Strand Invasion and Amplification Example 8 describes the development of FRET probe chemistry for monitoring invasion and amplification of target DNA. The chemistry allows simultaneous monitoring of the invasion process that takes place in both terminal regions of the target duplex. This is also a confirmatory method to ensure that the full length of target DNA was amplified. Primers and invasion oligonucleotides are labelled with fluorophores and quenchers respectively to form a fluorescence resonance energy transfer (FRET) system as shown in FIG. 9A. The primers which determine the terminal region of the target duplex are labelled with a fluorophore at the 5'-end or internally (different fluorophore for the forward and reverse primer). The invasion oligonucleotide that binds to the downstream terminal of the target DNA is labelled with a quencher at the 3'-end while the invasion oligonucleotide that binds to the downstream terminal of the target DNA is labelled with a quencher at the 5'-end.

A standard amplification reaction using the parallel configuration was conducted as described in Example 1 except that 5% PEG 1000 was replaced with 7.5% PEG 400. 200 nM of an invasion oligonucleotide labelled with a quencher close to its 5'-end (SEQ ID NO: 21) and 200 nM of an invasion oligonucleotide labelled with a quencher at the 3'-end (SEQ ID NO: 22) were used. The forward primer (SEQ ID NO: 23) and reverse primer (SEQ ID NO: 24) with internally labelled fluorophore ROX and Cy5 respectively were used at 200 nM. These oligonucleotides were used to amplify a target DNA (SEQ ID NO: 17). Real-time detection of amplification was performed by using a Bio Rad CFX 96 PCR device. The signals were measured after each cycle for 120 cycles (each cycle equals 30 seconds) and signals reported as relative fluorescence unit (RFU).

Figure 9B:
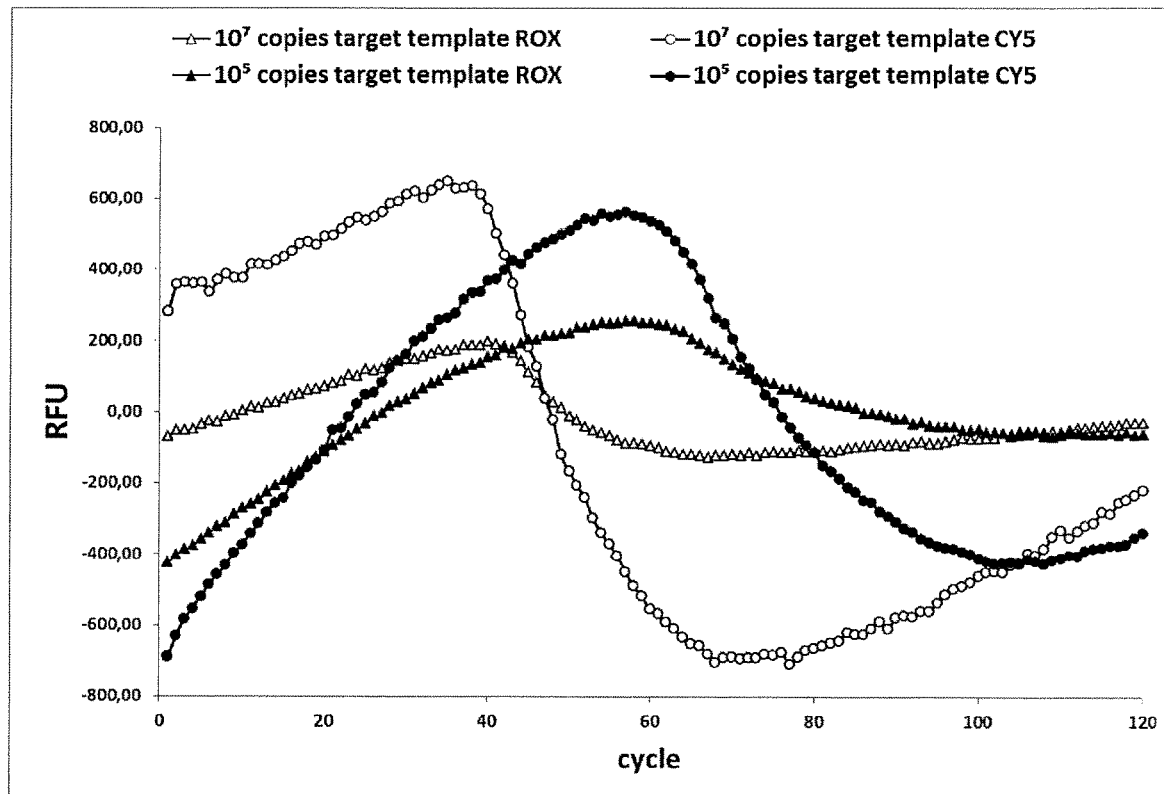

FIG. 9B shows the signal profile of the FRET system during amplification of the target template (SEQ ID NO: 17). During the reaction, the terminal regions of the amplicon become incorporated with different fluorophores. The upstream region in this case will incorporate the ROX fluorophore while the downstream region incorporates the Cy5 fluorophore. During invasion of the amplicon, the fluorophore signal emitted decreased (since the invasion oligonucleotides labelled with quencher became in close proximity with the terminal region of the amplicon) as seen in FIG. 9B. The simultaneous decrease in signal emitted by the forward and reverse primers suggested that both primers were incorporated into the amplicon

Example 9 Sensitivity of Multiple Invasion System

Figure 10A:
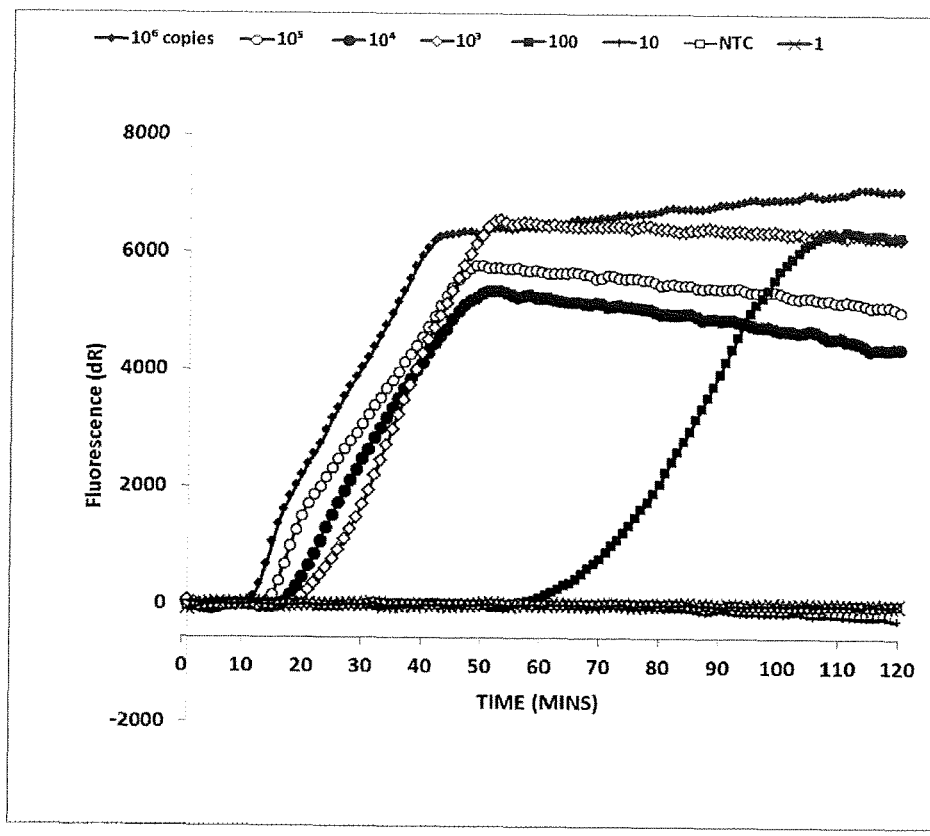
FIG. 10: Sensitivity of strand invasion based amplification using two strand invasion oligonucleotides. Sensitivity was assessed with three different assays using serial dilutions of $10^6$ to 1 copy of target DNA. Real-time monitoring of target DNA amplification was achieved using Sybr green I. Amplification plots: (a) Assay 1 (b) Assay 2 and (c) Assay 3. X-axis): Time (minutes). Y-axis: fluorescence of Sybr green I (arbitrary units).
Figure 10B:
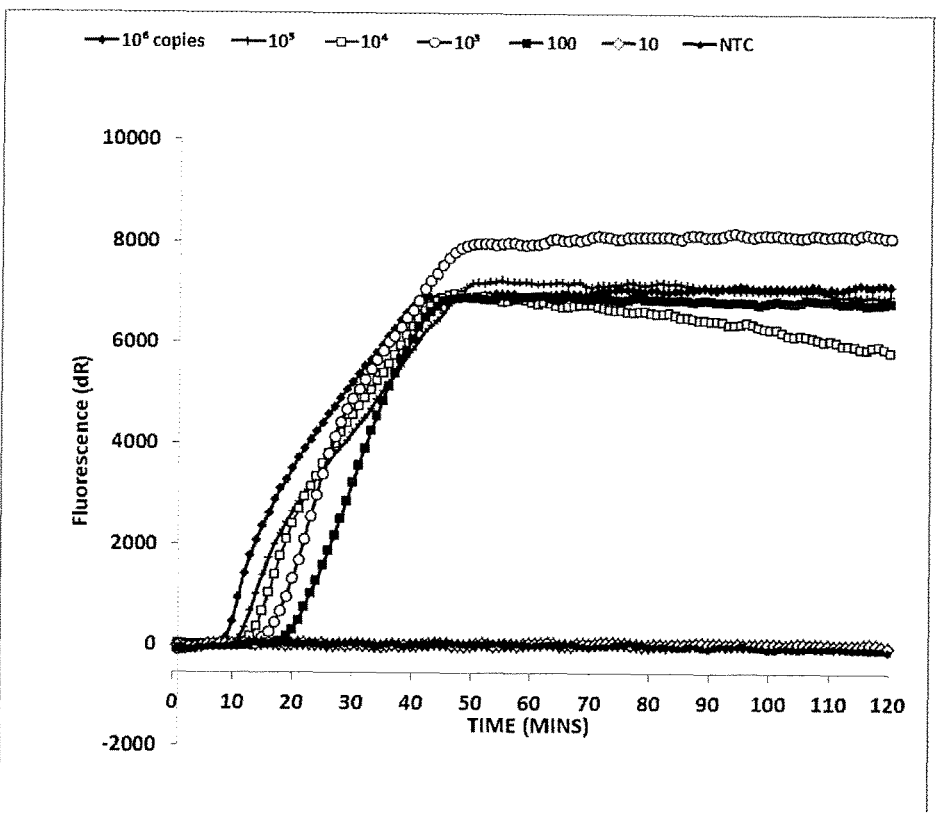
Figure 10C:
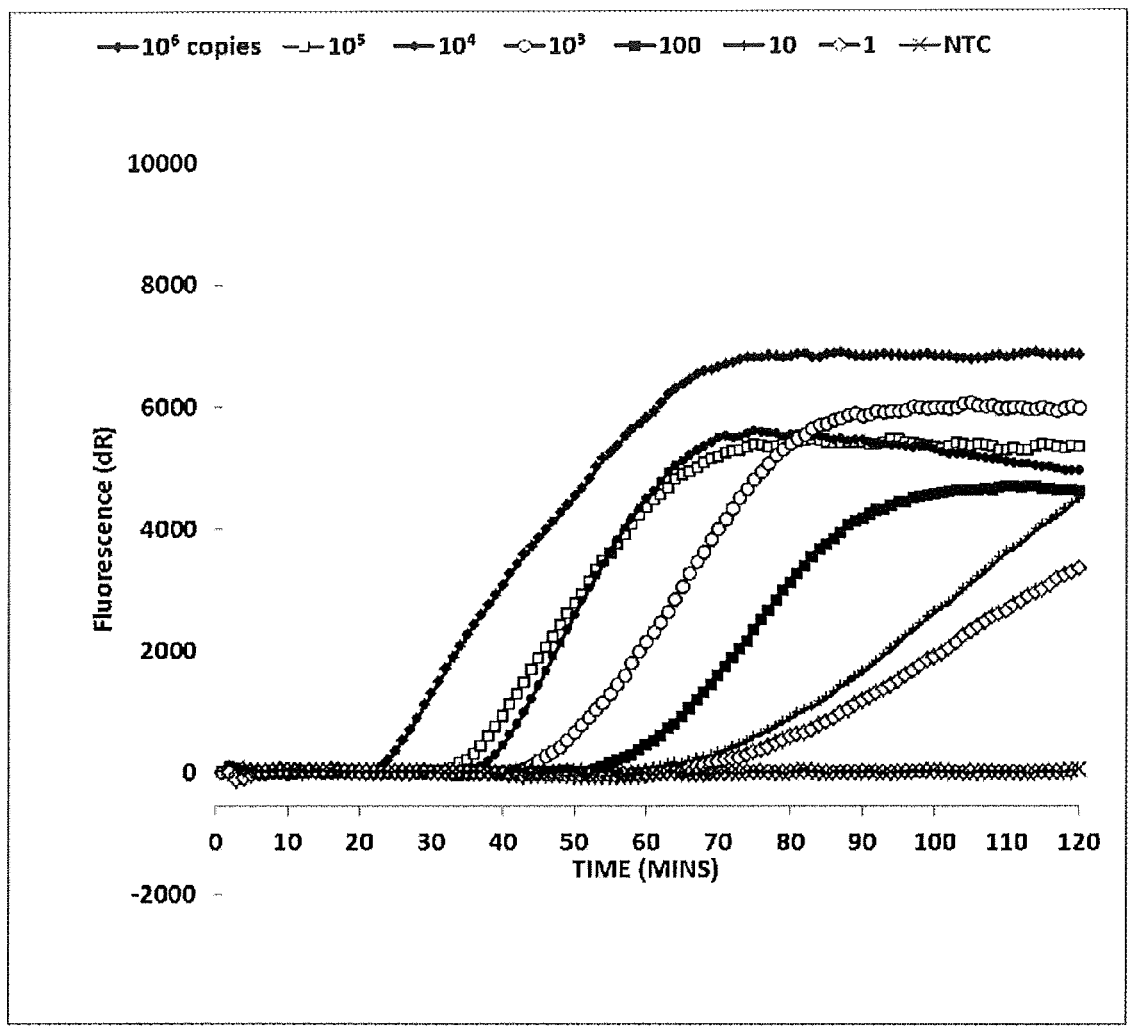

In this example, the analytical sensitivity of three different assays was evaluated. A standard amplification reaction was conducted as described in Example 1 except that 5% PEG 1000 was replaced with 7.5% PEG 400. Assays 1, 2 and 3 were used to amplify target DNA 1 (SEQ ID NO: 16), target DNA 2 (SEQ ID NO: 17) and target DNA 3 (SEQ ID NO: 18) respectively. The oligonucleotides as well as their concentrations used were as described in Example 7. A tenfold serial dilution for target DNA from $10^6$ copies to 1 copy was tested. The results are presented in FIG. 10. All three assays were sensitive to at least 100 DNA target copies (Assay 1, 2 and 3 are shown in FIGS. 10A, 10B and 10C respectively). Assay 3 showed in some experiments sensitivity to detect even a single copy of target DNA (FIG. 11C).

The invention claimed is:

1. A method for amplification of a nucleic acid sequence of unknown sequence, wherein said nucleic acid sequence is flanked by an upstream binding region comprising a first adaptor sequence and a downstream binding region comprising a second adaptor sequence, the method comprising contacting a nucleic acid comprising said nucleic acid sequence, under appropriate conditions, with:
   (a) a first strand invasion oligonucleotide having a non-extendible 3' termini;
   (b) a second strand invasion oligonucleotide having a non-extendible 3' termini; and
   (c) primers comprising an upstream primer and a downstream primer, wherein said primers are capable of amplifying the nucleic acid sequence,
   wherein said first strand invasion oligonucleotide binds to said first adaptor sequence and said second strand invasion oligonucleotide binds to said second adaptor sequence, thereby rendering the upstream binding region and the downstream binding region single-stranded to allow binding of said primers, wherein the appropriate conditions are isothermal conditions and include the presence of a recombinase, wherein the method comprises strand invasion at two sites through binding of said first strand invasion oligonucleotide to said first adaptor sequence and said second strand invasion oligonucleotide to said second adaptor sequence, wherein said upstream and downstream binding regions are present in opposing strands of said nucleic acid, and wherein said first strand invasion oligonucleotide and said second strand invasion oligonucleotide are configured to bind to said nucleic acid in an antiparallel orientation.

2. The method according to claim 1, wherein the upstream and downstream binding regions are present in the same strand of the nucleic acid.

3. The method according to claim 1, wherein the upstream and downstream binding regions are present in opposing strands of the nucleic acid with their 3'ends directed towards each other.

4. The method according to claim 3, wherein said first invasion oligonucleotide and said second strand invasion oligonucleotide are configured to bind to the opposing strands of the nucleic acid with their 3'ends directed away from each other.

5. The method according to claim 1 wherein the upstream binding region and/or the downstream binding region of the nucleic acid does not overlap with binding region for the respective upstream or downstream primer.

6. A method of amplifying a target nucleic acid sequence of unknown sequence comprising creating a nucleic acid sequence comprising upstream and downstream strand invasion oligonucleotide binding regions flanking said target nucleic acid sequence of unknown sequence, said binding sequences each incorporating an adaptor sequence, and amplifying said target nucleic acid sequence by carrying out the method according to claim 1.

7. A method of determining the sequence of a target nucleic acid of unknown sequence, comprising creating a nucleic acid sequence comprising upstream and downstream strand invasion oligonucleotide binding regions flanking said target nucleic acid sequence of unknown sequence, said binding sequences each incorporating an adaptor sequence, amplifying said target nucleic acid sequence by carrying out the method according to claim 1, and determining the sequence of said region of unknown sequence.

8. The method according to claim 7, wherein said first strand invasion oligonucleotide and said second strand invasion oligonucleotide have identical sequences.

9. The method according to claim 1, wherein the nucleic acid sequence is greater than 100 nucleotides in length.

10. The method according to claim 1, wherein said first strand invasion oligonucleotide and said second strand invasion oligonucleotide have different sequences.

11. The method according to claim 1, wherein the first adaptor sequence and the second adaptor sequence are identical sequences.

12. The method according to claim 1, wherein the first adaptor sequence and the second adaptor sequence are different sequences.

13. The method according to claim 1, wherein the upstream primer and the downstream primer have identical sequences.

14. The method according to claim 1, wherein the upstream primer and the downstream primer have different sequences.

* * * * *